(12) United States Patent
Phillips et al.

(10) Patent No.: US 9,551,706 B2
(45) Date of Patent: Jan. 24, 2017

(54) DENSITY-BASED METHODS FOR SEPARATION OF MATERIALS, MONITORING OF SOLID SUPPORTED REACTIONS AND MEASURING DENSITIES OF SMALL LIQUID VOLUMES AND SOLIDS

(75) Inventors: Scott T. Phillips, Cambridge, MA (US); George M. Whitesides, Newton, MA (US); Katherine A. Mirica, Cambridge, MA (US); Emanuel Carrilho, Chestnut Hill, MA (US); Andres W. Martinez, Cambridge, MA (US); Sergey S. Shevkoplyas, Brighton, MA (US); Phillip W. Snyder, Ringgold, PA (US); Raquel Perez-Castillejos, Cambridge, MA (US); Malancha Gupta, Cambridge, MA (US); Adam Winkleman, Somerville, MA (US); Katherine L. Gudiksen, San Francisco, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 1248 days.

(21) Appl. No.: 12/666,132

(22) PCT Filed: Jun. 30, 2008

(86) PCT No.: PCT/US2008/068797
§ 371 (c)(1),
(2), (4) Date: Jul. 8, 2010

(87) PCT Pub. No.: WO2009/006409
PCT Pub. Date: Jan. 8, 2009

(65) Prior Publication Data
US 2010/0285606 A1 Nov. 11, 2010

Related U.S. Application Data

(60) Provisional application No. 60/947,214, filed on Jun. 29, 2007, provisional application No. 60/952,483, (Continued)

(51) Int. Cl.
*G01N 33/553* (2006.01)
*G01N 33/543* (2006.01)
(Continued)

(52) U.S. Cl.
CPC ..... *G01N 33/5434* (2013.01); *B01L 3/502761* (2013.01); *G01N 33/54333* (2013.01);
(Continued)

(58) Field of Classification Search
CPC .................. B01L 3/502761; B01L 3/502776; B01L 3/50825; B01L 2200/0652; B01L 2300/045; B01L 2300/0877; B01L 2300/089; B01L 2400/043; B01L 2400/0457; B01L 2400/0487; G01R 33/1269; G01N 33/54333; G01N 33/5434
(Continued)

(56) References Cited

U.S. PATENT DOCUMENTS 4,049,398 A 9/1977 Vaseen
4,062,765 A 12/1977 Fay et al.
(Continued)

FOREIGN PATENT DOCUMENTS

EP 0571858 A1 12/1993
WO WO-2005085131 9/2005
(Continued)

OTHER PUBLICATIONS

Purcell, E. "Electricity and Magnetism," Berkeley Physics Course, vol. 2, Second Edition, 1985, ISBN 0-07-004908-4, 497 pages.
(Continued)

*Primary Examiner* — Mark Shibuya
*Assistant Examiner* — Pensee Do
(74) *Attorney, Agent, or Firm* — Wilmer Cutler Pickering Hale and Dorr LLP

(57) ABSTRACT

The ability to levitate, to separate, and to detect changes in density using diamagnetic particles suspended in solutions containing paramagnetic cations using an inhomogeneous magnetic field is described. The major advantages of this separation device are that: i) it is a simple apparatus that does not require electric power (a set of permanent magnets and gravity are sufficient for the diamagnetic separation and collection system to work); ii) it is compatible with simple optical detection (provided that transparent materials are used to fabricate the containers/channels where separation occurs; iii) it is simple to collect the separated particles for further processing; iv) it does not require magnetic labeling of the particles/materials; and v) it is small, portable. The method and kits provided provide for separation and collection of materials of different densities, diagnostics for detection of analytes of interest, monitoring of solid-supported chemical reactions and determination of densities of solid and liquid mixtures.

49 Claims, 25 Drawing Sheets

Related U.S. Application Data filed on Jul. 27, 2007, provisional application No. 61/039,983, filed on Mar. 27, 2008.

(51) Int. Cl.
*B01L 3/00* (2006.01)
*G01R 33/12* (2006.01)
*B01D 35/06* (2006.01)

(52) U.S. Cl.
CPC ...... *G01R 33/1269* (2013.01); *B01L 3/50825* (2013.01); *B01L 3/502776* (2013.01); *B01L 2200/0652* (2013.01); *B01L 2300/045* (2013.01); *B01L 2300/089* (2013.01); *B01L 2300/0877* (2013.01); *B01L 2400/043* (2013.01); *B01L 2400/0457* (2013.01); *B01L 2400/0487* (2013.01)

(58) Field of Classification Search
USPC .......................................... 436/526; 210/695
See application file for complete search history.

(56) References Cited

U.S. PATENT DOCUMENTS

| | | | |
|---|---|---|---|
| 4,508,625 A * | 4/1985 | Graham | ........................ 210/695 |
| 4,957,939 A | 9/1990 | Gries et al. | |
| 6,902,065 B2 | 6/2005 | Kimura et al. | |
| 7,008,572 B2 | 3/2006 | Kimura et al. | |
| 2002/0022276 A1 | 2/2002 | Zhou et al. | |
| 2002/0153295 A1 | 10/2002 | Kimura et al. | |
| 2002/0197622 A1 | 12/2002 | McDevitt et al. | |
| 2003/0219785 A1 | 11/2003 | Hallahan et al. | |
| 2004/0002169 A1 * | 1/2004 | Kraus et al. | ................. 436/526 |
| 2004/0009614 A1 | 1/2004 | Ahn et al. | |
| 2004/0072278 A1 | 4/2004 | Chou et al. | |
| 2005/0274650 A1 | 12/2005 | Frazier et al. | |

FOREIGN PATENT DOCUMENTS

| | | |
|---|---|---|
| WO | WO-2005105314 | 11/2005 |
| WO | WO-2007035498 | 3/2007 |
| WO | WO-2009006409 | 1/2009 |

OTHER PUBLICATIONS

Watarai et al., "Magnetophoretic Fractionation of Microparticles in Aqueous Media in Capillary Flow System", Analytical Sciences 2001, vol. 17 Supplement, pp. i169-i171, 3 pages.

Beaugnon, et al., "Levitation of Organic Materials," Nature, vol. 349, Feb. 1991, pp. 470.

Brandt, E. H., "Levitation in Physics," Science, vol. 243, No. 4889, Jan. 1989, pp. 349-355.

Catherall, et al., "Cryogenically Enhanced Magneto-Archimedes Levitation," New Journal of Physics, 7, 2005, 118, 10 pages.

Catherall, et al., "Floating Gold in Cryogenic Oxygen," Nature, vol. 422, Apr. 2003, pp. 579.

Catherall, et al., "Separation of Binary Granular Mixtures Under Vibration and Differential Magnetic Levitation Force," Physical Review E 71, 2005, pp. 021303-1-021303-8.

Choi, et al., "An Integrated Microfluidic Biochemical Detection System for Protein Analysis with Magnetic Bead-Based Sampling Capabilities," Lab Chip, 2002, 2, pp. 27-30.

Feinstein, et al., "Three-Dimensional Self-Assembly of Structures Using the Pressure Due to a Ferrofluid in a Magnetic Field Gradient," Journal of Applied Physics 99, 2006, pp. 064901-1-064901-6.

Franzreb, et al., "Protein Purification Using Magnetic Adsorbent Particles," Appl. Microbiol. Biotechnol., 2006, 70, pp. 505-516.

Furdui, et al., "Immunomagnetic T Cell Capture from Blood for Pcr Analysis Using Microfluidic Systems," Lab Chip, 2005, 4, pp. 614-618.

Gates, et al., "New Approaches to Nanofabrication: Molding, Printing, and Other Techniques," Chem. Rev., 2005, 105, pp. 1171-1196.

Geim, et al., "Magnet Levitation at your Fingertips," Nature, vol. 400, Jul. 1999, pp. 323-324.

Gijs, M., "Magnetic Bead Handling On-Chip: New Opportunities for Analytical Applications," Microfluid Nanofluid, 2004, 1, pp. 22-40.

Haukanes, et al., "Application of Magnetic Beads in Bioassays," Bio/Technology, vol. 11, Jan. 1993, pp. 60-63.

Hirota, et al., "Magneto-Archimedes Levitation and its Application," Riken Review No. 44, Feb. 2002, pp. 159-161.

Hirota, et al., "Magneto-Archimedes Separation and Its Application to the Separation of Biological Materials," Physica B 346-347, 2004, pp. 267-271.

Ikezoe, et al., "Making Water Levitate," Nature, vol. 393, Jun. 1998, pp. 749-750.

Ikezoe, et al., "Separation of Feeble Magnetic Particles with Magneto-Archimedes Levitation," Energy Conversion and Management 43, 2002, pp. 417-425.

Ikezoe, et al., "Stable Levitation of Water by Magneto-Archimedes Principle," Transactions of the Materials Research Society of Japan, 2000, 25 [1], pp. 77-80.

Inglis, et al., "Microfluidic High Gradient Magnetic Cell Separation," Journal of Applied Physics 99, 2006, pp. 08K101-1-08K101-3.

International Search Report and Written Opinion of the International Searching Authority, the United States Patent and Trademark Office, for International Application No. PCT/US2008/068797, dated Dec. 31, 2008, 13 pages.

Islam et al., "Detection of Shigella dysenteriae Type 1 and Shigella flexneri in Feces by Immunomagnetic Isolation and Polymerase Chain Reaction," Journal of Clinical Microbiology, vol. 30, No. 11, Nov. 1992, pp. 2801-2806.

Ito, et al., "Review: Medical Application of Functionalized Magnetic Nanoparticles," Journal of Bioscience and Bioengineering, vol. 100, No. 1, 2005, pp. 1-11.

Jayawant, B. V., "Electromagnetic Suspension and Levitation," Rep. Prog. Phys., vol. 44, 1981, pp. 411-477, 74 pages.

Jayawant, B. V., "Review Lecture: Electromagnetic Suspension and Levitation Techniques," Proc. R. Soc. Lond., a 416, pp. 245-320, Apr. 1988.

Kimura, "Study on the Effect of Magnetic Fields on Polymeric Materials and Its Application," Polymer Journal, vol. 35, No. 11, pp. 823-843, 2003.

Kimura, et al., "Micropatterning of Cells Using Modulated Magnetic Fields," Langmuir 2005, 21, pp. 830-832.

Kimura, et al., "Separation of Solid Polymers by Magneto-Archimedes Levitation," Chemistry Letters 2000, pp. 1294-1295.

(56) References Cited

OTHER PUBLICATIONS

Lee, et al., "Solvent Compatibility of Poly(dimethylsiloxane)-Based Microfluidic Devices," Anal. Chem., 2003, 75, pp. 6544-6554.
Lund et al., "Assessment of Methods for Covalent Binding of Nucleic Acids to Magnetic Beads, Dynabeads™, and the Characteristics of the Bound Nucleic Acids in Hybridization Reactions," Nucleic Acids Research, vol. 16, No. 22, 1988, pp. 10861-10880.
Lyuksyutov, et al., "Trapping Microparticles with Strongly Inhomogeneous Magnetic Fields,". Midern Physics Letters B., vol. 17, No. 17, 2003, pp. 935-940.
McCarty, et al., "Self-Assembly: Electrostatic Self-Assembly of Polystyrene Microspheres by Using Chemically Directed Contact Electrification," Agnew. Chem. Int. Ed., 2007, 46, pp. 206209.
Meldal et al., "Direct Visualization of Enzyme Inhibitors using a Portion Mixing Inhibitor Library Containing a Quenched Fluoregenic Peptide Substrate. Part 1. Inhibitors for Subtilisin Carlsberg," J. Chem. Soc. Perkin Trans., Jan. 1995, pp. 1591-1596.
Ng, et al., "Review: Components for Integrated Poly(dimethylsiloxane) Microfluidic Systems," Electrophoresis, 2002, 23, pp. 3461-3473.
Oberteuffer, J., "Magnetic Separation: A Review of Principles, Devices, and Applications," IEEE Transactions on Magnetics, vol. MAG-10, No. 2, Jun. 1974, pp. 223-238.
Pamme, et al., "On-Chip Free-Flow Magnetophoresis: Continuous Flow Separation of Magnetic Particles and Agglomerates," Anal. Chem., 2004, 76, pp. 7250-7256.
Pamme, N., "Magnetism and Microfluidics," Lab Chip, 2006, pp. 24-38.
Raj, et al., "Invited Paper: Commerical Applications on Ferrofluids," Journal of Magnetism and Magnetic Materials, 85, 1990, pp. 233-245.
Raj, et al., "New Commercial Trends of Nanostructured Ferrofluids," Indian Journal of Engineering & Materials Sciences, vol. 11, Aug. 2004, pp. 241-252.
Safarik et al., "Review: Use of Magnetic Techniques for the Isolation of Cells," Journal of Chromatography B,. 722, 1999, pp. 33-53.
Shipway, et al., "Investigations into the Electrostatically Induced Aggregation of Au Nanoparticles," Langmuir, 2000, 16, pp. 8789-8795.
Sia, et al., "Analytical Methods: an Integrated Approach to a Portable and Low-Cost Immunoassay for Resource-Poor Settings," Agnew. Chem. Int. Ed., 2004, pp. 498-502.
Simon, et al., "Diamagnetic Levitation: Flying Frogs and Floating Magnets (invited)," Journal of Applied Physics, vol. 87, No. 9, May 2000, pp. 6200-6204.
Squires, et al., "Microfluidics: Fluid Physics at the Nanoliter Scale," Reviews of Modern Physics, vol. 77, Jul. 2005, pp. 977-1026.
Supplemental European Search Report and Written Opinion for European Patent Application No. 08826080 dated Jan. 25, 2011, 14 pages.
Watarai, et al., "Capillary Magnetophoresis of Human Blood Cells and their Magnetophoretic Trapping in a Flow System," Journal of Chromatography A, 961, 2002, pp. 3-8.
Watarai, et al., "Magnetophoretic Behavior of Single Polystyrene Particles in Aqueous Manganese(II) Chloride," Analytical Sciences, Oct. 2001, vol. 17, pp. 1233-1236.
Weibel, et al., "Bacterial Printing Press that Regenerates its Ink: Contact-Printing Bacteria Using Hydrogel Stamps," Langmuir, 2005, 21, pp. 6436-6442.
Winkleman, et al., "A Magnetic Trap for Living Cells Suspended in a Paramagnetic Buffer," Applied Phuysics Letters, vol. 85, No. 12, Sep. 2004, pp. 2411-2413.
Xia, et al., "Soft Lithography," Agnew. Chem. Int. Ed., 1998, 28, pp. 551-575.
Yager, et al., "Microfluidic Diagnostic Technologies for Global Public Health," Nature, vol. 442, Jul. 2006, pp. 412-418.
Yamato, et al., "Levitation Polymerization to Fabricate a Large Polymer Sphere," Langmuir 2002, 18, pp. 9609-9610.
Yamato, Novel Strategies for Fundamental Innovation in Polymer Science, 2005, pp. 123-139, ISBN: 81-308-0060-8, Published by Research Signpost, Editor Naofumi Naga.

\* cited by examiner

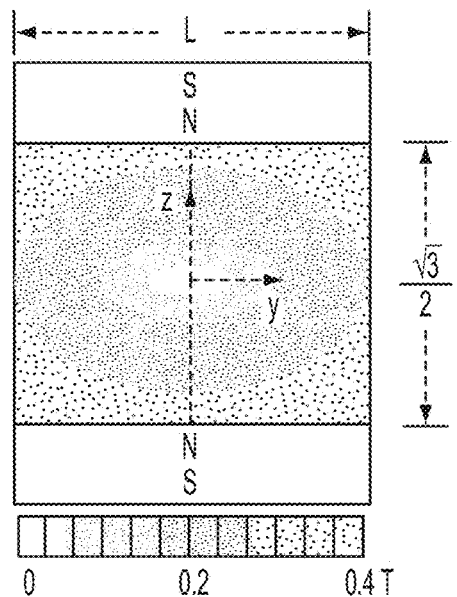 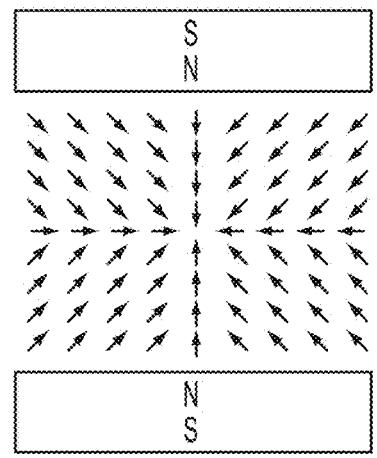
FIG. 1A  FIG. 1B
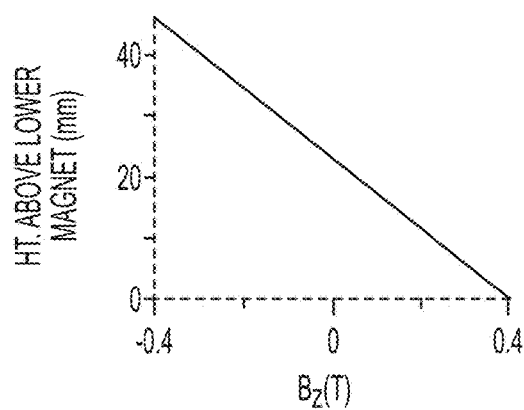
FIG. 1C

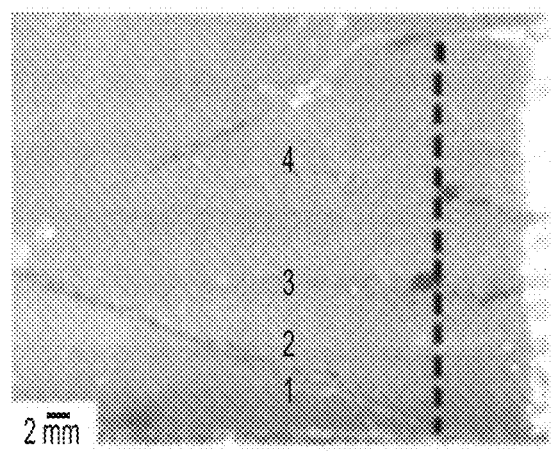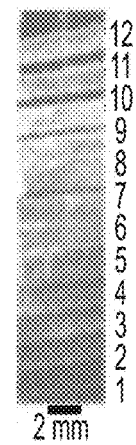
FIG. 23A          FIG. 23B
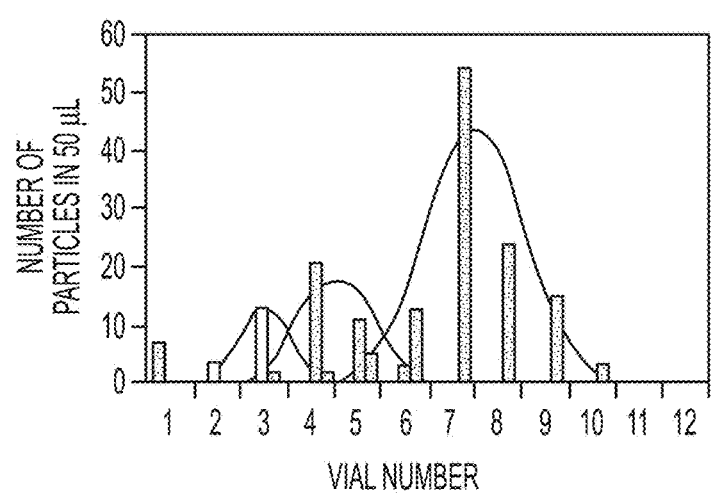
FIG. 23C

DENSITY-BASED METHODS FOR SEPARATION OF MATERIALS, MONITORING OF SOLID SUPPORTED REACTIONS AND MEASURING DENSITIES OF SMALL LIQUID VOLUMES AND SOLIDS

RELATED APPLICATIONS

This application claims the benefit of priority under 35 C.F.R. §119(e) to the following applications:

U.S. Provisional Application No. 60/947,214, filed Jun. 29, 2007, entitled "Microfluidic Device for Detecting and Separating Diamagnetic Materials";

U.S. Provisional Application No. 60/952,483, filed Jul. 27, 2007, entitled "Density-Based Magnetic Separation";

U.S. Provisional Application No. 61/039,983, filed Mar. 27, 2008, entitled "Density-Based Methods For Monitoring Of Solid Supported Reactions And Measuring Densities Of Small Liquid Volumes And Irregularly Shaped Solids," the contents of which are incorporated by reference in their entirety.

GOVERNMENT SUPPORT

This invention was made with Government support under grant No. GM065364 awarded by the National Institutes of Health and under grant No. N00014-01-1-0782 awarded by the Office of Naval Research. The Government has certain rights in the invention.

BACKGROUND

Magnetic labels facilitate the separation and purification of chemical and biological samples. These labels are often superparamagnetic nano- or microspheres (e.g., Invitrogen's Dynabeads™), which can be covalently attached to most chemical and biological samples. For example, immunomagnetic separation employs antibodies—often monoclonal—bound to magnetic particles for the removal of prokaryotic and eukaryotic cells from suspension. Many techniques—including cell separation, free flow magnetophoresis, and immunoassays—have been developed for use in microfluidic devices for lab-on-a-chip technology. These magnetic labeling techniques have several limitations: i) the separations are binary: magnetic particles are separated from diamagnetic particles; ii) the labeling of a diamagnetic material requires a chemical reaction; iii) the presence of a magnetic particle attached to a diamagnetic material—specifically a cell, antibody, or protein—alters the functionality and properties of the surface of the material; and iv) the magnetic label must be removed after separation to obtain a pure diamagnetic sample.

In the last decade, the magnetic levitation of diamagnetic materials has become more accessible to standard laboratory facilities as the early experimental setup consisting of superconducting magnets (>10 T) and a pressurized oxygen atmosphere has been replaced by small rare-earth magnets and aqueous paramagnetic salt solutions. One of the characteristics of magnetic levitation is that there is only one position in a magnetic field in which an object is stably levitated. When a levitating object in magnetic fields is moved away from a position of equilibrium, a restoration force on the object returns it to equilibrium position. This stable point is determined by its volume magnetic susceptibility and density. Therefore, different substances levitated in the same magnetic field have different equilibrium positions of levitation and can thus be separated.

As an extension of levitation, diamagnetic traps have been developed to control, manipulate, and direct the positioning of cells and polymer microspheres suspended in solution. Magnetic field maxima can exist only at the source of the field and therefore stable trapping of materials having greater magnetic susceptibility than their environments occurs at the source of the field. Magnetic field minima can be achieved outside or spaced a distance from a magnetic field source. The magnetic minima have been used to levitate and confine biological materials and other diamagnetic materials. For example, in microfluidic systems, diamagnetic particles suspended in ferrofluid or an aqueous paramagnetic solution have been trapped and their trajectory manipulated while traversing the inhomogeneous magnetic fields.

Magnetic separations are used extensively in biomedicine, and other areas, usually in systems that separate magnetic particles (or magnetically-labeled particles) from diamagnetic media. Magnetic media has also been used to separate diamagnetic particles, with ferrofluids providing the largest magnetic response.

A variety of sensors are available for measuring densities of liquids and solids.

For liquids, floating bulb hydrometers estimate density values with accuracies of ±0.01 g/cm$^3$. This method is simple, portable, and does not require electricity for measuring densities of large volumes of fluids (>10 mL). Pycnometers are more accurate ($\rho$=±0.001-0.0001 g/cm$^3$), but lack portability. Pycnometers require accurate measurements of both mass and volume of the sample and, therefore, are highly dependent on the availability and accuracy of an analytical balance. It also requires milliliter volumes of fluid to obtain an accurate measurement of volume. Density measurements with accuracies of ±0.00001 g/cm$^3$ can be obtained using oscillating-tube density meters. This technology uses a resonating glass or metal tube of fixed volume; the density of the liquid filling the tube can be determined through its relationship to the resonant frequency of the tube. These instruments cost several thousand dollars, but offer the desirable characteristics of portability (by using batteries as the source of energy), automation, high-throughput, and the ability to process volumes of 1-5 mL. Recently, Sparks and co-workers have developed a lab-on-a-chip version of this device that is capable of measuring density values of liquids using volumes as small as 0.5 μL.

Hydrostatic weighing is a common technique for measuring densities of solids. It relies on the Archimedes principle and requires an accurate measurement of both the mass of the solid and the volume of the liquid that it displaces on the hydrostatic balance. This technique is useful for relatively large solids that produce detectable changes in volume upon submersion. Pycnometers also can be used for measuring densities of solids. The weight of the solid is obtained using an analytical balance and the volume is carefully measured by the amount of liquid that the solid displaces within the pycnometer. Density-gradient columns are a standard and accurate method for measuring densities of solids—usually plastics—with non-uniform shapes and with sensitivities of ±0.0001 g/cm$^3$. This method operates on observations of the level to which a sample sinks in a column of liquid containing a density gradient. The mass and volume of the sample does not need to be measured accurately. The method, however, is time consuming (several hours per measurement) and requires the use of expensive standards with known densities.

SUMMARY

Label-free separations of diamagnetic, materials that differ in density are described. Systems and methods that exploit the principle of diamagnetic levitation to observe changes in density due to biological, chemical, or electrostatic binding events are described. Methods to separate and collect diamagnetic materials with different densities using a microfluidic system are also provided. The system and methods are suitable for use in the separation and collection of materials that differ in density, or as a diagnostic for detecting molecular or colloidal binding to polymer microspheres, the density of which becomes modified by the binding events.

In other aspects, label-free techniques for manipulating, sorting, analyzing and/or measuring diamagnetic materials in suspension are described. Systems and methods that exploit the principle of diamagnetic levitation to monitor solid-supported chemical reactions or measure densities of difficult to measure samples, such as small liquid volumes and irregularly-shaped solids are provided.

The basis for the separation of materials is the balance of the magnetic and an opposing force, e.g., gravitational forces on diamagnetic materials suspended in a paramagnetic medium. The protocols for detection and separation require only a paramagnetic fluid, e.g., a solution of gadolinium salt, although any paramagnetic salt could be used instead, two magnets, and (optionally) a simple diagnostic device, e.g., a scale or an imaging device. Separation may also be based, in principle, on the combination of magnetic forces with forces other than gravity.

In one aspect, a method of detecting insoluble particles or materials based on differences in density, includes providing a solution comprising a paramagnetic salt in a solvent; exposing a material having a first density to a density modifying agent to form a modified material having a second density; and applying a magnetic field to the paramagnetic solution, said solution comprising at least the modified material, wherein the unmodified material and the modified material occupy different positions in the magnetic field.

In one or more embodiments, the modified material is covalently associated with the density modifying agent.

In one or more embodiments, the material is a polymer particle having a chemically reactive site and the density modifying agent is an organic molecule capable of reacting at the polymer particle reactive site.

In one or more embodiments, the reactive site is at the surface of the particle or the polymer particle is porous and the reactive site is in an internal volume of the particle.

In one or more embodiments, the density modifying agent comprises a plurality of density modifying agents, each capable of reaction at the polymer particle reactive site and each providing a modified particle having a density different from that of the unmodified particle and from each other.

In one or more embodiments, the modified material is non-covalently associated with the density modifying agent, and optionally, the non-covalent association is selected from the group consisting of electrostatic, hydrophobic, hydrophilic, ionic and van der Waals attractive associations.

In one or more embodiments, the material comprises a particle including a surface-bound biomolecule and the density modifying agent is a small molecule that binds to the biomolecule, or the material comprises a particle including a surface-bound organic moiety and the density modifying agent is a biomolecule that binds to the organic moiety. Optionally, the binding is specific.

In one or more embodiments, the material comprises a charged particle, and optionally, the density modifying agent comprises a colloidal particle of opposite charge, wherein the density of the charged particle and the colloidal particles are different, and for example, the colloidal particles comprise heavy metal particles.

In one or more embodiments, the material comprises a particle and the density modifying agent comprises an organic moiety linked to the particle.

In one or more embodiments, the density modifying agent comprises a plurality of organic moieties of different densities and wherein the paramagnetic solution comprises a plurality of modified particles having different densities.

In one or more embodiments, the paramagnetic solution is an aqueous solution or a non-aqueous solution, or a gadolinium(III) salt, such as for example, gadolinium(III) diethylenetriamine triacetic acid tetradecane.

In one or more embodiments, the material comprises a particle having a particle size in the range of about 5-5000 μm, and optionally, the particles are substantially monodisperse.

In one or more embodiments, the magnetic field is linear in a direction along an axis between two magnets generating the magnetic field, and for example, the magnetic field gradient is constant.

In another aspect, a label-free method of detecting an analyte of interest includes providing a solution comprising a paramagnetic salt in a solvent, said solution comprising a polymer bead functionalized for specific binding with an analyte of interest; exposing the paramagnetic solution to a sample of interest; exposing the paramagnetic solution to a magnetic field; and detecting the presence of the analyte of interest by detecting a change in position of the polymer bead in the magnetic field.

In one or more embodiments, the paramagnetic solution comprises a population of polymer beads functionalized for specific binding with a plurality of analytes, wherein the presence of a particular analyte is detected by a change in the position of the polymer bead to a new position characteristic of the particular analyte, and for example, the analyte is selected from the group consisting of proteins, peptides, organic molecules, nucleic acids, oligonucleotides, antibodies, antigens, sugars and carbohydrates.

In one or more embodiments, the population of polymer beads have the same density or the population of polymer beads have different densities.

In one or more embodiments, the material comprises a particle having a particle size in the range of about 5-5000 μm, and optionally the particles are substantially monodisperse.

In one or more embodiments, the magnetic field is linear in a direction along an axis between two magnets generating the magnetic field, and for example, the magnetic field gradient is constant.

In another aspect, a microfluidic system for detecting and separating diamagnetic particles or materials includes means for generating a magnetic field; a fluid flow chamber positioned between the magnetic field generating means, said chamber having an inlet for introducing fluid on a first inlet side of the fluid flow chamber and a plurality of outlet conduits positioned substantially adjacent to one another on a second outlet side of the fluid flow chamber, wherein fluid flows from inlet conduit towards the plurality of outlet conducts; and collectors for receiving fluid from each of the outlet conduits, wherein the magnetic gradient is along a direction that is substantially orthogonal to the direction of a fluid flow, wherein the chamber expands along a dimension of the magnetic gradient from the inlet side to the outlet side.

In one or more embodiments, the microfluidic device further includes an injector for housing and introducing fluid into the chamber, and for example, the injector is a pressure injector or a gravity injector.

In one or more embodiments, the microfluidic device further includes a port for introducing a particle-containing solution into the chamber.

In one or more embodiments, the system is configured and arranged to provide laminar fluid flow.

In one or more embodiments, the chamber extends from the inlet conduit in a substantially triangular shape.

In one or more embodiments, the means for generating a magnetic field comprises permanent magnets, superconducting magnets and electromagnets, and optionally, magnetic field is varies linearly in a direction along an axis between magnetic poles and, for example, the magnetic field gradient is constant.

In another aspect, a method of separating particles based on differences in density includes providing a separating solution comprising a paramagnetic salt in a solvent; introducing an individual particle or a plurality of particles into the separating solution, each particle comprised a polymer core, and a density modifying agent, the agent selected from a group of organic moieties differing systematically by an R-group; and applying a magnetic field having a magnetic gradient to the separating solution, wherein the particles occupy different locations in the magnetic field based upon the density modifying agent.

In one or more embodiments, the polymer cores are of substantially the same compositions having substantially the same density, the polymer cores are of different composition and have different densities.

In another aspect, a method of label-free detection of binding of a molecule of interest based on differences in density includes providing a separating solution comprising a paramagnetic salt in a solvent; introducing a plurality of particles into the separating solution, the particles comprising one of a host linked to the particle; exposing the particles to one of a guest that is capable of binding to the host linked to the particles; and applying a magnetic field having a magnetic gradient to the separating solution, wherein the particles occupy different equilibrium locations within the magnetic field based on whether a binding complex is formed.

In another aspect, a label-free method of detecting an analyte of interest includes exposing a polymer bead functionalized for specific binding with an analyte of interest to a sample of interest; introducing the functionalized polymer bead into a solution comprising a paramagnetic salt in a solvent; exposing the paramagnetic solution to a magnetic field; and detecting the presence of the analyte of interest by detecting a change in position of the polymer bead in the magnetic field.

In one or more embodiments, introduction of the functionalized polymer bead into the paramagnetic solution occurs before exposing the functionalized beads to the sample of interest.

In one or more embodiments, wherein introduction of the functionalized polymer bead into the paramagnetic solution occurs after exposing the functionalized beads to the sample of interest.

In one or more embodiments, the host is selected from the group consisting of proteins, peptides, nucleic acids, organic molecules, inorganic molecule, oligonuceotides, sugars, polysaccharides, antibodies and antigens, and optionally, the guest is selected from the group consisting of proteins, peptides, nucleic acids, organic molecules, inorganic molecule, oligonuceotides, sugars, polysaccharides, antibodies and antigens, wherein the guest is capable of forming a binding complex with the host.

In one aspect, a method of monitoring a solid phase chemical reaction includes providing a solution comprising a paramagnetic salt in a solvent; introducing a plurality of particles into the solution, the particles functionalized with a reactive moiety capable of chemical reaction; initiating a chemical reaction on the functionalized particles; applying a magnetic field having a magnetic gradient to the solution during or after the chemical reaction; and noting the position of the functionalized particles in the solution, wherein said position is an indicator of the extent of reaction and/or the composition of a reaction product.

In another aspect, a method of monitoring a solid phase chemical reaction includes providing a plurality of particles, the particles functionalized with a reactive moiety capable of chemical reaction; initiating a chemical reaction on the functionalized particles; introducing a reacted or partially reacted particle into a solution comprising a paramagnetic salt in a solvent; applying a magnetic field having a magnetic gradient to the solution; and noting the position of the reacted or partially reacted particle in the paramagnetic solution, wherein said position is an indicator of the extent of reaction and/or the composition of a reaction product.

In one or more embodiments, portions of particles are removed at selected times during reaction and the position of the functionalized particle is an indication of extent of reaction.

In one or more embodiments, the paramagnetic salt comprises gadolinium(III) diethylenetriamine triacetic acid tetradecane and, optionally, the solvent comprises an organic solvent.

In one aspect, a method of measuring the density of a liquid or a solid includes providing a paramagnetic solution comprising a paramagnetic salt in a solvent; introducing a solid or a solvent-immiscible liquid into the paramagnetic solution; applying a magnetic field having a magnetic gradient to the separating solution and allowing the solid or liquid to levitate at a position in the paramagnetic solution relative to the magnetic field; providing a calibration curve that correlates levitation height with density; and comparing the levitation height of the unknown solid or solvent-immiscible liquid with the calibration curve to determine the density of the unknown solid or solvent-immiscible liquid.

In one or more embodiments, the solvent-immiscible liquid comprises a solute dissolved in a solvent, or the solid is irregularly shaped.

In one or more embodiments, the solvent-immiscible liquid is urine and the density of the urine correlates to a physiological condition, and optionally, the physiological condition is body hydration.

In one or more embodiments, the solvent-immiscible liquid is blood and the density of the blood correlates to a physiological condition.

In still another aspect, a method of determining mixture composition includes providing a paramagnetic solution comprising a paramagnetic salt in a solvent; introducing a solvent-immiscible liquid or solid mixture into the paramagnetic solution; applying a magnetic field having a magnetic gradient to the paramagnetic solution and allowing the liquid or solid mixture to levitate at a height in the paramagnetic solution; providing a calibration curve that correlates levitation height with solute concentration for a range of solute concentrations in the liquid or solid mixture; and comparing the levitation height of the unknown solvent-immiscible liquid or solid mixture with the calibration curve to determine the solute concentration in the unknown solvent-immiscible liquid or solid mixture.

In one or more embodiments, the solute is water and the liquid is fuel and the method determines the water content of fuel.

In one or more embodiments, the solute is a saccharide or alcohol and the liquid is a beverage and the method determines the sugar or alcohol content of the beverage.

In still another aspect, a kit includes a paramagnetic salt; and a population of polymer beads, said bead functionalized for specific binding with an analyte of interest, and optionally, the polymer beads are functionalized for binding a biomolecule, and for example, the biomolecule is selected from the group consisting of proteins, peptides, nucleic acids, polynucleic acids, oligonucleotides, sugars, polysaccharides, antigens and antibodies.

In one or more embodiments, the paramagnetic salt is soluble in organic solvents, and for example, the paramagnetic salt comprises gadolinium(III) diethylenetriamine triacetic acid tetradecane.

In one or more embodiments, the kit further includes a cuvette or sample holder for housing the polymer beads.

In one or more embodiments, the kit further includes instructions for use in detecting a formation of a binding complex between the functionalized polymer bead and an analyte of interest.

In another aspect, a kit for determining the density of a biological fluid sample includes a paramagnetic salt that is soluble in an organic solvent; and a calibration curve relating the density of a biological fluid with a density.

In one or more embodiments, the biological fluid is urine and the density of the urine correlates to a physiological condition and, for example, the physiological condition is body hydration.

In one or more embodiments, the biological fluid is blood and the density of the blood correlates to a physiological condition.

In another aspect, a kit includes a cuvette comprising paramagnetic salt solution; and a liquid sample withdrawer for obtaining a droplet of oil from an engine or motor; and an indicator to indicate whether oil should be changed.

The simplicity and versatility of these methods make them useful for general laboratory protocols. They are also suitable for use in remote locations where electricity is not available and where portability and operational ease are essential. These density-based detection and separation methods have the potential to be widely useful as analytical tools for the physical and biological sciences.

Monitoring conversion of reactions on polymer supports using differences in density provides an alternative to more complex methods that require instruments like FTIR, NMR (with a magic-angle spinning probe), high-performance liquid chromatography, or mass spectrometry. The technique does not require electricity and the device occupies the same bench space as a hot-plate. The method is useful as a quick screen for determining when a reaction has reached its endpoint, and is similar to TLC for solution phase chemistry.

Measuring densities of both liquids and solids according to one or more embodiments is inexpensive, rapid, sensitive, and portable should be useful for many applications that require accurate measurements of density, and that do not necessarily require precise knowledge of the chemical composition of the sample.

BRIEF DESCRIPTION OF THE DRAWING

FIG. 1 is a schematic representation (A) of the magnetic field, (B) the distribution of magnetic forces, and (C) a graph of the calculated magnitude of magnetic field along the axis of the magnets used for separation.

FIG. 23 contains photographs of four Merrifield resins with different amounts of chloromethyl functionality separated in the magnetic apparatus shown in FIG. 21. The degree of functionality of the spheres from the bottom to the top of the channel is (1) 1.95, (2) 1.24, (3) 1.06 and (4) 0.38 mmol of Cl/g of polymer. A) An image of a flowing separation in a microfluidic device. The flow goes from left to right and the beads are separated by the magnetic field and collected in the twelve outlet channels on the right. The dotted line is the location in the channel over the center of the magnets. B) An image of the outlet tubing several centimeters downstream near the conclusion of the experiment illustrating successful separation and collection of the particles. C) A histogram of a sample population of beads collected from the vial attached to each outlet tube as labeled in (B), illustrating the successful separation and collection of spheres that differ in density.

DETAILED DESCRIPTION

Figure 2:
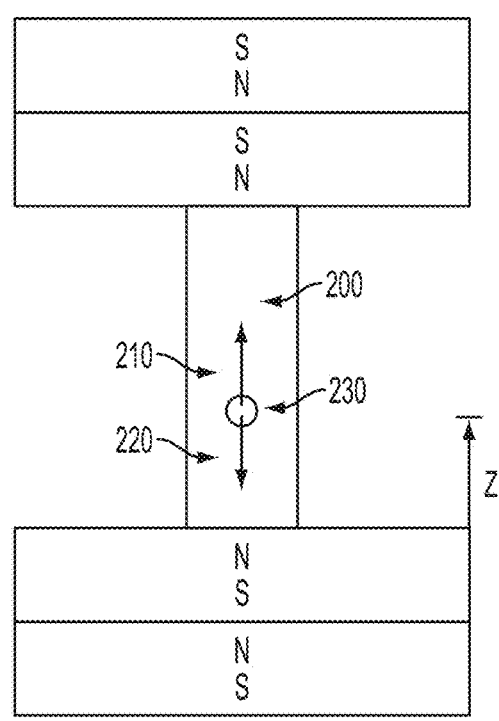
FIG. 2 is a schematic illustration of a device for determining the location of a diamagnetic particle in paramagnetic solution exposed to a magnetic force.

The principle of magnetic levitation involves subjecting materials of having different densities in a fluid medium (or which develop different densities over time) having paramagnetic or superparamagnetic properties (a separating solution) to an inhomogeneous magnetic field. The magnetic field generates a non-uniform pressure equivalent to the magnetic energy density in the fluid. This pressure exerts a net force on the particles in the fluid that is independent of the particles and in a direction opposite to the gradient of the magnetic field. By applying the magnetic field in such a manner that the force on the particles is opposed by another uniform force, e.g., the force of gravity, thereon, a balance is achieved for particles that is directly related to their density. Thus, particles of higher density will 'sink' when placed in the magnetic field and particles of lower density will 'float' until they reach a location of equilibrium where opposing forces are balanced. This phenomenon can be used to detect particle composition, density, and other properties based on their characteristic location in a magnetic fluid.

As described in greater detail herein, compounds that exhibit very subtle differences in density occupy a unique location in a magnetic field at equilibrium. This difference may be used to separate materials of different densities, to identify the presence of a specific material or analyte, to monitor solid supported chemical reactions and to determine the density and composition of solids, liquids and solutions or other mixtures. In one or more embodiments, particles with differences in density of no more than 0.05 g/cm³, or even densities with accuracies of ±0.0001 g/cm³ are detected or distinguished. Higher resolution is expected with optimization of the methods and systems according to one or more embodiments. In one or more embodiments, differences in density are used to detect and/or distinguish between particles with and without surface modification, among molecules having different functional groups, or between complexed and uncomplexed conjugates. Changes in levitation height also are used to indicate a binding event and the presence of an analyte, or to monitor the progress of a chemical reaction.

Principles of Material Characterization by Magnetic Levitation

Density-based separations of diamagnetic materials are determined by the balance between the magnetic force and the buoyant force on a diamagnetic particle in a paramagnetic solution. In a static system, the force per unit volume (F/V) on a particle in a magnetic field is the sum of the gravitational and magnetic forces (Equation 1), $$\vec{F}/V = -(\rho_l - \rho_p)\vec{g} - \frac{(\chi_l - \chi_p)}{\mu_0}(\vec{B}\cdot\vec{\nabla})\vec{B} \quad (1)$$

where the density of the liquid is $\rho_l$, the density of the particle is $\rho_p$, the acceleration due to gravity is g, the magnetic susceptibilities of the liquid and the particle are $\chi_l$ and $\chi_p$, respectively, the magnetic permeability of free space is $\mu_0$, and the local magnetic field is $\vec{B}=(B_x, B_y, B_z)$. Both the magnetic field and its gradient contribute to the magnetic force and are optimized according to the dimensions of the system in order to maximize the separation. Equation 1 can be simplified for the levitation of a point particle—i.e., an infinitesimally small particle—in a system at equilibrium in which the magnetic field only has a vertical component ($B_z$); that is, the two other normal components of the applied magnetic field ($B_x$ and $B_y$) are zero (Equation 2).

$$(\rho_l - \rho_p)g = \frac{(\chi_l - \chi_p)}{\mu_0}B_z\frac{\partial B_z}{\partial z} \quad (2)$$

The distribution of magnetic field is determined by the size, geometry, orientation, and nature or type of the magnets as illustrated in FIG. 1A. The calculated value of the magnitude of the magnetic field, $|\vec{B}|$, of the system is shown for a set of magnets, 50-mm long (L), separated by a distance defined by $\sqrt{3}(L/2)\approx$ of approximately 43 mm. The shading in the plot indicates the magnitude of the magnetic field; the darker regions correspond to higher field intensities (white ~0 T and black is ~0.4 T). This field was calculated using a finite element modeling software under axisymmetric boundary conditions. In one or more embodiments, a set of solid-state NdFeB magnets may be employed. In specific embodiments, NdFeB magnets with length, width, and height of 5 cm, 5 cm, and 2.5 cm, respectively, having a magnetic field of ~0.4 T at their surface, were used to generate the required magnetic field and magnetic field gradient. Two magnets oriented towards each other in the design of an anti-Helmholtz coil established the magnetic field distribution in our system. In this geometry, the $B_x$ and $B_y$ components of the magnetic field are exactly zero only along the axis of the magnets, that is, along the vertical dashed line in FIG. 1A, as confirmed by the completely vertical orientation of the force along this axis. FIG. 1B illustrates the distribution of magnetic forces on diamagnetic material within a paramagnetic solution. The calculation shows that a diamagnetic particle would be repelled from the surfaces of the magnets and would be trapped along the axis between the magnets. The $B_z$ component of the magnetic field also becomes zero over this axis, but only at the midpoint between the two magnets. The effect of the magnetic force in this geometry is to attract the paramagnetic solution towards one or the other of the two magnets and, as a consequence, to trap all diamagnetic particles at the central region between the magnets (FIG. 1B)—i.e., where B is close to zero.

For this particular configuration, when the distance between the two magnets is $\sqrt{3}$ times the length of the magnets, the magnetic field profile is approximately linear, and the gradient of the magnetic field is approximately constant in the z-direction (FIG. 1C). FIG. 1C is a graph of the calculated magnitude of the magnetic field in the vertical direction, Bz, along the axis between the two magnets (the dotted line in FIG. 1A); the direction of a positive z-vector was chosen to be toward the upper magnet. The other components of the magnetic field along the chosen path are zero. Note that the gradient of the magnetic field in the vertical direction is constant—i.e., a constant slope in the variation of the magnetic field along the axis. Thus, particles of different densities will align themselves along the z-axis in predictable spacings. An exemplary system is illustrated in FIG. 2. A magnetic solution 200 is disposed between two magnets. Magnetic force and gravity are indicated by arrows 210, 200 illustrating the opposing direction of these two forces. A diamagnetic particle 230 will reach an equilibrium position within the magnetic field. In one or more embodiments, this configuration is used for separating many materials that differ in density.

In one or more embodiments, the solution has a positive magnetic susceptibility. The solvent used for the liquid solution should not dissolve the materials to be separated. Typical liquids include water and other polar organic solvents, such as methanol, ethanol isopropanol, butanol, N,N-dimethylformamide, dimethylsulfoxide, and N-methylpyrolidinone, however non-polar organic solvents can also be used. The density of solvent will play a role in the materials that can be separated. For example, by selecting a solvent that is more or less dense than the particles to be separated, the particles will either sink or float prior to exposure to the magnetic field gradient. Solvent density may be selected such that all the particles float or sink prior to the separation process. The solubility of the paramagnetic salt in the solvent is also a consideration.

A paramagnetic salt is added to form the paramagnetic solution. Aqueous or organic solutions of magnetic inorganic salts may be used. Exemplary salts include salts based on the lanthanide cations, manganese chloride, manganese sulfate, iron chloride, iron sulfate, gadolinium chloride, gadolinium chelate salts and the like. The magnetic susceptibility of the paramagnetic organic salt solutions is approximately proportional to concentration. The spatial resolution depends, in part, on the density of the materials to be separated, the density of the supporting solution, the magnetic susceptibility of the paramagnetic salt, along with the constant gradient ($\partial B_z/\partial z$) of the magnetic system used. The closer the density of the separating solution matches the densities of the materials to be separated, the smaller the concentration of magnetic salt that is required for separation. Similarly, the higher the magnetic susceptibility of the magnetic salts, the less is required to achieve separation. In typical embodiments, concentrations ranging from 0.05 M-2.0 M are suitable.

In certain embodiments, a gadolinium salt is used. Exemplary $Gd^{3+}$ salts include $GdCl_3$, gadolinium(III)(diethylenetriaminepentaacetic acid) (Gd(DTPA)) and (gadolinium (III) diethylenetriamine triacetic acid tetradecane (Gd $(DT_3)$). There are at least four characteristics of $Gd^{3+}$ cations that make them useful for detection of density differences: i) they (along with some of the other lanthanide cations)

possess the largest magnetic susceptibilities ($\chi=+0.028$ cm$^3$/mol GdCl$_3$) of any ionic species; ii) they permit straightforward visualization of samples because their solutions are colorless; iii) they are compatible with proteins and cells when chelated (e.g., Gd$^3$ DTPA complex); and iv) they have acceptable cost (salts of Gd$^{3+}$ can cost <\$0.34/g salt=<\$0.80/g Gd$^{3+}$=<\$125.8/mol Gd$^{3+}$), and the solutions are reusable.

In a specific embodiment, a paramagnetic aqueous solution of Gd$^{3+}$ (gadolinium(III) diethylenetriamine triacetic acid tetradecane (Gd(DT$_3$)) is used. In one embodiment, the chelating ligand is readily accessible and binds tightly to Gd$^{3+}$ to minimize the Lewis acidity of Gd$^{3+}$. Gadolinium-DTPA satisfies these requirements, and is well suited for aqueous paramagnetic solutions as it is insoluble in most organic solvents. The diethylenetriamine triacetic acid tetradecane ligand Gd(DT$_3$) enhances solubility in a wide range of organic solvents and the DT$_3$ ligand (like DTPA) nearly fills the coordination sphere of Gd$^{3+}$, thus reducing the Lewis acidity of the Gd$^{3+}$ species. The lower acidity reduces the reactivity of the metal center. Exemplary solvents for Gd(DT$_3$) include methanol, toluene, benzene, N,N-dimethylformamide, pyridine, anisole, water, 2-fluorotoluene, benzonitrile, fluorobenzene, nitroethane, dimethylsulfoxide, chlorobenzene, 2,4-difluorotoluene, 1-chloro-2-fluorobenzene, dichloromethane, bromobenzene, chloroform, carbon tetrachloride, perfluoro(methyl decalin), and diiodomethane. The Gd(III) complex is soluble in organic solvents and can, for example, be used to follow the progress of solid-phase reactions using magnetic levitation. The ready solubility of Gd(DT$_3$) in organic solvents facilitates tuning of the system to increase the sensitivity of the method; this feature is especially useful for reactions that lead to small changes in density between the starting polymer and the final product. The Gd(III) complex is only weakly Lewis acidic and can be used to monitor solid-supported reactions in real time.

Since $\chi_p$ is negligible for all diamagnetic materials ($\chi_p \approx 0$), the magnetic force on a diamagnetic object is linearly proportional to the magnetic susceptibility of the paramagnetic solution ($\chi_d$ in Equation 2). Gd$^{3+}$ generates a large magnetic force for a given concentration of cations and value of applied magnetic field than other transition metal cations. The large magnetic susceptibility of Gd$^{3+}$ (compared, for example, to the susceptibilities of other lanthanide cations), enables the system to levitate particles with greater density for an equal concentration of paramagnetic cations, and/or to levitate a given particle using a lower concentration of paramagnetic ions.

Material Separations and Detection Using Magnetic Levitation

A system and method for detecting and/or separating diamagnetic materials based on differences in density are described. In one or more embodiments, diamagnetic particles (>ca. 5 μm in diameter) may be separated based on differences in density. In one or more embodiments, particles having ranging from about 5-5000 μm in diameter may be separated and/or detected. For particles smaller than 5 μm, more viscous solvents enable the stable levitation of even smaller particles.

Particles can vary in size over a wide range. In one or more embodiments, the particles are substantially monodisperse. Particles of different size may vary somewhat in density, so that the particles may distribute over a distance in the paramagnetic fluid. Particles with a narrower particle size distribution will provide more efficient separation and will provide more concentrated levitation in the magnetic field.

In one embodiment, a static mode—using no flow of fluid—is used as a diagnostic for detecting molecular or colloidal binding to polymer microspheres. In another embodiment, a flowing (dynamic) mode (within a microfluidic device) is used as a tool for continuously collecting separated diamagnetic particles. The technique is useful for purifying large quantities of samples since continuous flow and separation are possible. Several devices also may be linked in parallel to improve resolution with minimal extra cost. The type of separation presented here will be useful in remote settings and in resource-poor regions: the system requires no electricity, the apparatus and paramagnetic solutions are reusable, and the readout is accomplished by eye.

The systems (in either mode) require only simple components that include solutions of paramagnetic salts, such as Gd$^{3+}$ salts, sandwiched between a set of magnets. Any magnetic setup may be used, including for example, electromagnets, permanent magnets, and superconducting magnets and the like. In one or more embodiments, permanent magnets, e.g., rare earth magnets, are used, such alike those shown in FIG. 1A and in FIG. 2, where z indicates the vertical direction. Permanent magnets may be used in operations or applications that may be conducted outside a medical or laboratory facility—e.g., in remote locations where electricity is not available or where portability is a desirable feature.

Any bead or particle of regular or irregular shape may be used, provided that it is diamagnetic and of a density that permits its displacement in a magnetic field. Suitable materials are not soluble in the solvent and do not swell to any considerable extent in the solvent. In some embodiments, the material is a polymer and the polymer is capable of surface chemical modification. Exemplary polymer particles include particles made up of polystyrene, polypropylene, polyethylene, a Tentagel resin, an Argopore resin, polyethylene glycol (and copolymers of), polyacrylamide, poly (methyl methacrylate), and others. Separation of the particles occur due to density differences arising from compositional differences in the particle core and the surface modifications.

Separation may be detected by visual inspection or under magnification, for example using an optical microscope. Other methods of detection, such as deflection of a beam of light, fluorescence of the polymers, visualization using a camera (and pattern recognition software) may be used.

In one or more embodiments, a microfluidic device is provided to enable the continuous collection of particles having different densities. The microfluidic device includes components on the order of micrometers to centimeters that are designed to handle fluid flow. The microfluidic device provides separation of materials of different density as the suspended materials continuously flow through the passages of the device. In some embodiments, a pump maybe used to maintain a fluid flow. In other embodiments, the microfluidic device can work without the need of electrical power (with gravity as the only pumping force of the system) thus providing a means for automating separation and collection processes at very high volumes (thousands of liters) while keeping the cost of the process extremely low, since the paramagnetic solution can be reused. This technique could be useful in recycling processes where different materials could be continuously separated as a function of their density and in processes that want to avoid the need of expensive reagents like antibodies.

Figure 21:
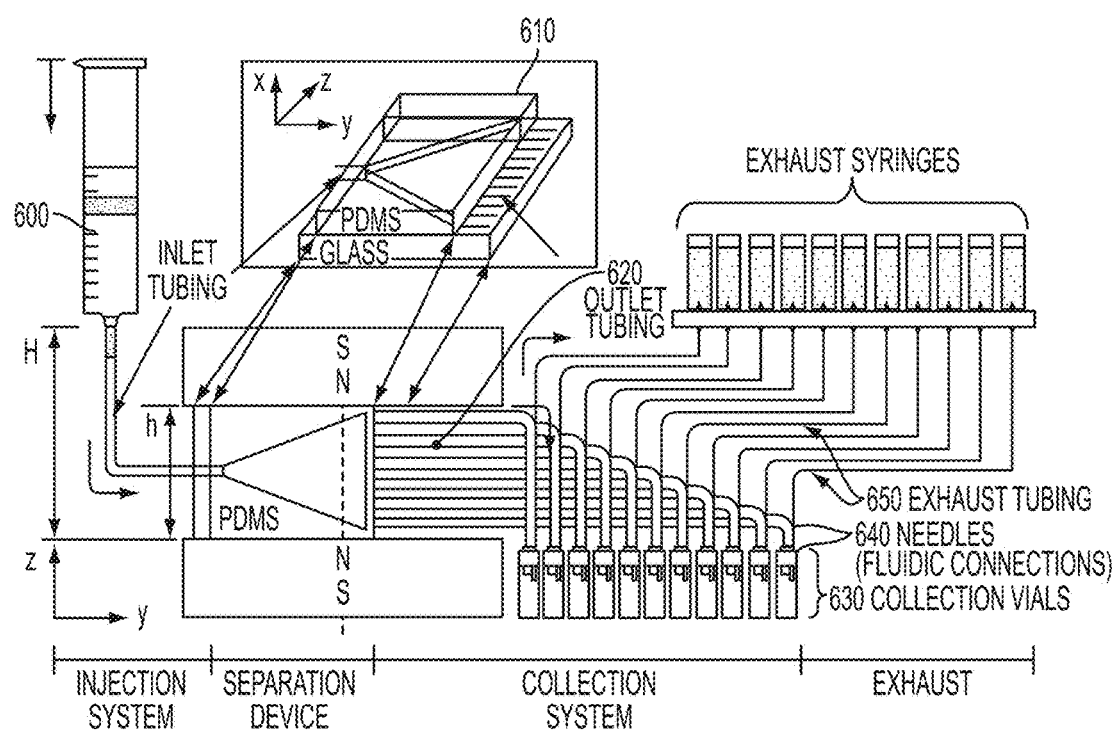
FIG. 21 is a schematic representation of the separation and collection system illustrating the four sections of the system: i) injection system, ii) separation device, iii) collection system, and iv) exhaust. A PDMS channel is placed between two permanent rare earth magnets with the direction of the fluid flow orthogonal (ŷ) to the direction of the poles of the magnets (ẑ) A triangular geometry for the channel was used to minimize the volume within the channel that experienced a minimal or zero flow rate. The inset highlights the PDMS chamber sealed to a glass slide, and shows both the inlet and the outlet tubing.

The microfluidic device takes advantage of laminar flow, that is, fluids flow in streams without turbulence that would disrupt separations. A microfluidic device for use according to one or more embodiments does not include magnetic components (except for magnets used to generate a magnetic field), provides for the continuous flow and separation of materials in dimensions ranging from a few micrometers to a few centimeters and is transparent or accessible to detection at the wavelengths used for detection. Microfluidic systems also use only small volumes of sample and solution. In one of the embodiments, the microfluidic device is positioned within two magnets and includes at least one channel that traverses the magnetic field generated by the magnets. The microfluidic system is made of a polymer that is inert to the fluid flowing within. The fluid containing particles to be separated flows into the channel that is disposed within the magnetic field. The particles are pumped into the chamber in a direction that is substantially orthogonal to the gradient of magnetic field. As the particles move into the channel (perpendicularly to the gradient of magnetic field), they also migrate in the direction of the magnetic field gradient to an equilibrium position of levitation in the chamber that is a function of the applied magnetic field, the magnetic susceptibility of the solution, and the particle density. The particles continue to flow through the chamber and pass at the opposite end into one of a plurality of outlet conduits that are positioned along the edge of the chamber in the direction perpendicular to that of the magnetic field gradient. The conduits collect the particles after they have been separated in the channel and into a collection vial. In this way, solutions enriched in a specific bead are obtained. See FIG. 21 for an illustration of an exemplary separation system. The device may be manually or automatically operated. In some embodiments, it may be computer-controlled. The device may be scaled to accommodate samples in a range of sizes and volumes. By changing the size of the separating chamber, the paramagnetic strength of the dynamic fluid and the size and strength of the magnetic field, samples of varying sizes, particle sizes and amounts may be separated.

Both a microfluidic system and a static system may be used to separate particles based on differences in density. In one or more embodiments, the principles of density-based separation are used to detect and distinguish between density-modified and unmodified polymers. By way of example, a polymer bead interacts or is modified through chemical, electrostatic, hydrophobic, hydrophilic, ionic, van der Waals or other means, with a density modifying agent to alter its density. The change in density is observable by the change in bead location in the paramagnetic fluid in a non-uniform magnetic field. Polymer beads that interact with or are modified by the density modifying agent exhibit a detectable difference in density from unmodified polymer beads.

In one or more embodiments a plurality of particles may be prepared that have a polymer core of substantially the same composition and a density modifying agent. The agent may be selected from a group of organic moieties differing systematically by an R-group. The R-group imparts a different density to each particle, allowing them to separate by magnetic levitation to different locations in a magnetic field The particles are introduced into a separating solution comprising a paramagnetic inorganic salt in a solvent, and a magnetic field having a magnetic gradient is applied to the separating solution, wherein the particles occupy different locations in the magnetic field based upon the density-modifying agent. In the case of the microfluidic system, the particles can traverse the magnetic field and exit the magnetic field at locations characteristic of their density, whereupon they may be collected as fractions substantially enriched in (or solely containing) a particle of a selected density. As the density is associated with a specific R-substituted polymer, the process effects the separation of beads with the same R-group.

In one or more embodiment, the bead is modified to include a surface-bound biomolecule, e.g., a protein, polynucleic acid, carbohydrate, and the like, and the density modifying agent is a small molecule that binds to the biomolecule. In one or more embodiments, the bead is modified with a small molecule that is capable of binding to a biomolecule, e.g., a protein. The binding may be specific—e.g., the protein binding site interacts preferentially and strongly with the small molecule. In this way, binding of a small molecule to the protein to form a small molecule-protein binding complex is an indication of the presence of the protein or small molecule in the analyte.

Figure 3A:
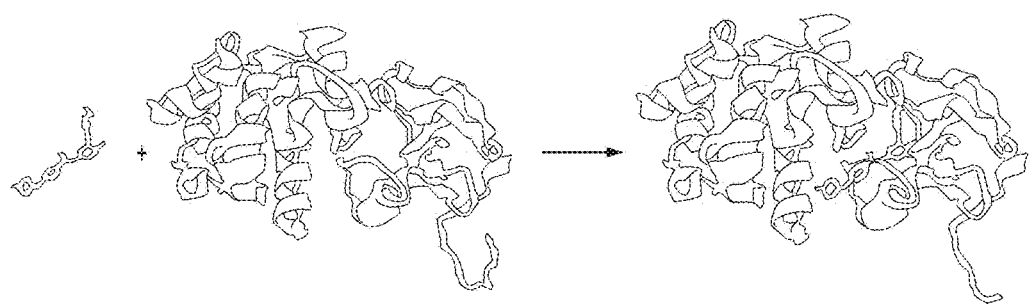
FIG. 3A is a schematic illustration of a biological binding event to demonstrate the change in density after binding.
Figure 3B:
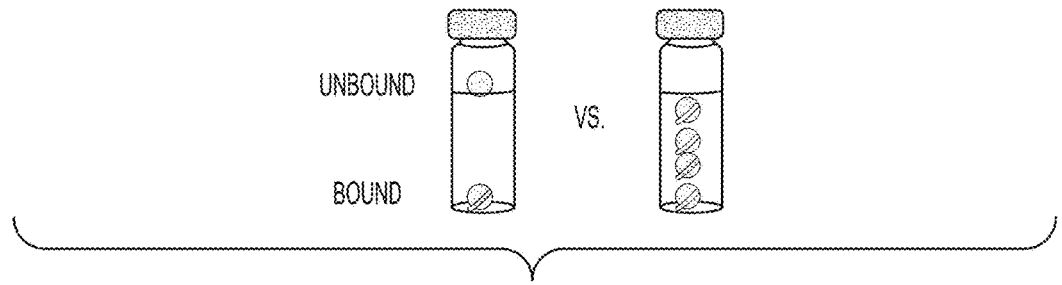
FIG. 3B is a schematic illustration of the separation of beads that have been bound to different ligands; the mass of the bound ligand determines the difference in density among the particles.

When a small molecule interacts non-covalently with a protein, it typically does so through protein surfaces providing favorable interactions with the small molecule. This interaction typically occurs without significant volume change, as is illustrated in FIG. 3. In FIG. 3A, a typical protein is shown having a mass of $mass_2$ which has a suitable binding site for a small molecule of $mass_1$. Once complexed, the protein-ligand complex has new, greater mass; however, the volume is effectively unchanged due to the efficient binding of the small molecule at the binding site. Thus, the density of, for example, an uncomplexed protein-modified polymer bead is expected to have a different density than a similar polymer bead having a protein-small molecule complex. This is illustrated in the left hand side illustration of FIG. 3B that shows the uncomplexed bead having a lower density than the complexed bead. The bead may be modified with multiple ligands, each capable of binding a different biomolecule and each complex having a different density, as illustrated the right hand side illustration in FIG. 3B.

This density-based detection should be applicable to other binding pairs: polymer-bound small molecule binding to a protein; polymer-bound protein binding to a small molecule; polymer-bound protein binding to another protein (e.g., antibody-antigen, or antigen-antibody, or protein-protein); polymer-bound nucleic acid binding to another nucleic acid (e.g., DNA-DNA, DNA-RNA, RNA-RNA); polymer-bound chemical receptor binding to an organic small molecule (<3000 molecular weight); and, polymer-bound chemical receptor binding to an inorganic compound or element.

In some embodiments, the polymer may be modified at the surface or through out the bead, e.g., in the internal volume of a porous bead. By modifying the bead interior, the bead loading is increased, which enhances the sensitivity of the bead in detections. In such an embodiment, the polymer bead is sufficiently porous that it can accommodate the receptor-small molecule complex within the bead. For example, the bead may be loaded with the small molecule and the polymer complexes to the small molecule-modified bead. The polymer internal spaces are of a size that permits access of the protein (or other binding moiety) to the interior of the polymer bead. Polymer loading may be achieved by any conventional method, for example, by exposing the beads to a solution containing the small molecule. By way of example, the polymer may be a biotin-labeled polymer bead and the protein may be streptavidin.

The principles of density-based separation are used to detect protein binding to small molecules without requiring the labeling of the protein or the small molecule. Identification of small molecules that bind specifically to proteins is an important aspect to the discovery and development of new drugs and to understanding complex physiological processes in the biological system. Accurate detection of small molecule binding (ligand-substrate binding) is important in many areas of scientific and technical endeavors.

In another example, the surface of the bead may be modified so that it is charged, i.e., negatively or positively charged. The density modifying agent may be an oppositely charged molecule or particle. Complexing may occur by ionic or electrostatic attraction. When the complexed bead has a density different from that of the uncomplexed bead, separation and/or detection may occur. By way of example, a polymer bead may be chemically modified to provide a surface with a positively charged moiety. A negatively charged molecule or a negatively charged nanoparticle, e.g., a particle that is smaller in diameter than the polymer particle, can interact by ionic attraction to form a new complex. If the density of the negatively charged nanoparticle is significantly different from that of the polymer particle, then the overall density of the complex is different. Thus, a polymer particle such as polystyrene, polyethylene, polypropylene, polyethylene glycol (or co-polymers of), and poly(methyl methacrylate) may be modified to provide a positive surface, for example with a tetraalkylammonium chloride functionality or guanidinium group. Gold nanoparticles can be functionalized, for example with a citrate layer, to provide a negative surface. When particles having a positive charge are exposed to the negatively charged gold particles, the gold particles assemble on the particle surface. Because gold is a much more dense material than the organic polymer, the overall density of the coated particle increases. Particles with and without the gold-bound particles will have different densities and are separable and detectable in a magnetic gradient. The coating may be accomplished with other materials than gold, provided that the density between the coating and bead is different. Methods of generating charged particles and charged colloidal particles or nanoparticles are well-known and may be used to prepare coated particles. Methods of detection based on interactions between charged species is not limited to colloids, and may be used for detecting metal salts, organophosphates (and other charged organic molecules), inorganic minerals, and other analytes that are charged.

In one or more embodiments, a plurality of particles, each modified by different small molecules, antigen, and the like, are used to identify a plurality of analyses (e.g., polymer that binds to the small molecule). The population of small-molecule modified polymer beads (or other appropriately modified beads) are exposed to a sample of interest, e.g., a biological sample. The presence of a specific analyte is detected by a change in the position of the modified beads to a new position that is characteristic of a specific small molecule-analyte complex. When a plurality of suitable modified beads are present, a plurality of different analytes may be detected.

In other embodiments, a single modified bead is used. The presence of an analyte of interest is indicated by the shift in the location of the bead from its uncomplexed position to a new position that is characteristic of the polymer bead complex.

The polymer beads can be treated to the sample of interest in the paramagnetic solution. However, under some circumstances, sensitive biomolecules may not be stable in the paramagnetic solution or it may not be optimal to conduct the binding operation in the paramagnetic solution. In one or more embodiments, polymer beads can be introduced into a biological sample and any binding that is to occur will occur in the sample of interest under favorable binding conditions. The polymer beads may then be removed and introduced into to the paramagnetic solution for magnetic-based density determination. By way of example, a blood sample or other physiological solution may be obtained and the functionalized beads can be introduced into a suitably prepared sample of the blood to allow for binding complex formation. The polymer beads can then be collected and introduced into the paramagnetic solution for density determination.

In some embodiments, the polymer bead is the same. In other embodiments, polymer beads of different compositions may be used. Polymer beads of different densities, each with different surface modifications, may be used to provide a greater range of detecting capabilities.

Monitoring Chemical Reactions on Solid Support or Solid Phase

Determining whether a solid-supported chemical reaction has reached completion (or has stopped progressing) is a difficult and tedious process, often requiring several steps and/or complex instruments (e.g., NMR, FTIR, and mass spectrometers). A rapid, inexpensive, and exceedingly sensitive method for monitoring conversion in solid-supported reactions in real time would simplify this process and would function as the equivalent of thin-layer chromatography (TLC) for solid-phase chemistry with no need for sampling.

Magnetic levitation method provides a powerful tool for developing chemistry on solid supports. Such a system can increase the efficiency and throughput of combinatorial chemistry, where solid phase chemistry is used frequently to generate lead compounds for drug development.

Techniques for monitoring the progress of solid-supported chemical reactions using magnetic levitation are described. The technique involves levitating a solid-supported starting material in a solution containing reagents for a reaction and a paramagnetic salt (i.e., Gd salts) in the presence of an external magnetic field. In one or more embodiments, $Gd(DT_3)$ is used in an organic solvent. The progress of a solid-supported reaction is visible in real time by the vertical position at which the polymer bead levitates. This vertical position reflects the density of the polymer and conversion in the reaction.

The principles of monitoring solid phase organic reactions should be useful to drug discovery programs, academic laboratories, and in any other applications where polymers are modified through chemical reactions. Typical methods for monitoring these types of solid phase reactions are either difficult or expensive. This method is simple, inexpensive, and the device is small and portable.

Figure 4:
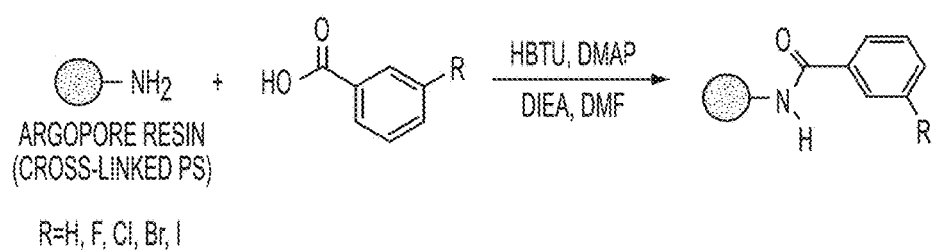
FIG. 4 illustrates a reaction scheme for the functionalization of an argopore bead with a halogen series R-group.
Figure 5:
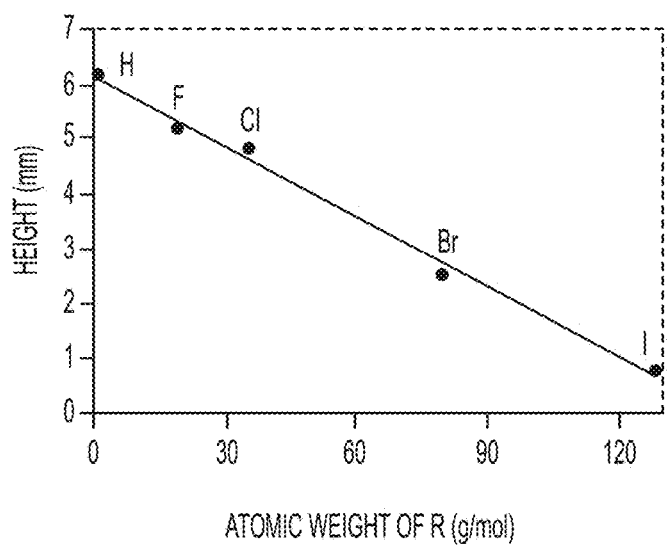
FIG. 5 is a plot of bead location (as measured as distance from a magnetic pole) as a function of molecular weight for the halogen substituted series of beads prepared as in FIG. 4.
Figure 6:
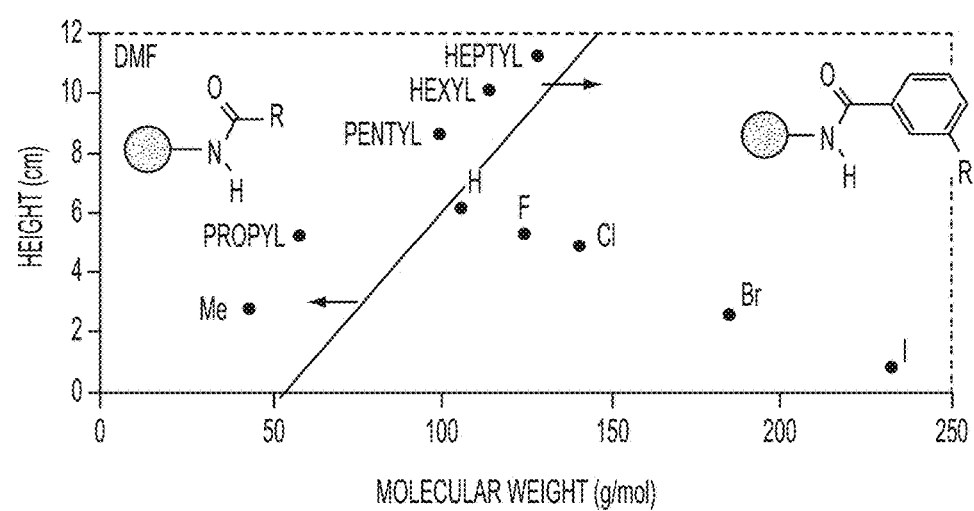
FIG. 6 is a plot of bead location (as measured as distance form a magnetic pole) as a function of molecular weight for two different bead series.

The following examples demonstrate the ability of the technique to detect small changes in chemical composition. A series of compositionally similar argopore (crosslinked polystyrene) beads modified with a specific surface functionalized R-group is shown in FIG. 4. To prepare a series of R-substituted beads, the beads are functionalized with a reactive group (here, an amino group—1.87 mmol $NH_2$/g of resin). The amino group is reacted with a series of m-functionalized benzoic acids to generate a series of beads with R=H, F, Cl, Br, I. In a magnetic field having a magnetic gradient, these beads demonstrate magnetic levitation and separation. The principle is illustrated in FIG. 5, in which the location (as measured by mm from one of the magnetic poles) of a series of m-substituted benzoate-functionalized argopore beads is displayed. The x-axis is molecular weight. The graph illustrates the measurable distance separating beads of different R-substitutions. This separation is most marked for the higher halides, where differences in size and density are more pronounced. Separation by magnetic levitation is useful over a wide range of R-functionalized polymer beads. FIG. 6 is a graph plotting the levitation height of two different R-group series versus molecular weight in a magnetic field having a magnetic gradient. The line separates the two series. On the left is the location data for a series of alkyl amide-substituted beads and on the right is the location data for a series of m-substituted benzoate-functionalized argopore beads with varied halide and alkyl substituents. Note that even R-groups with similar molecular weights can levitate at different location in a magnetic field.

Figure 7A:
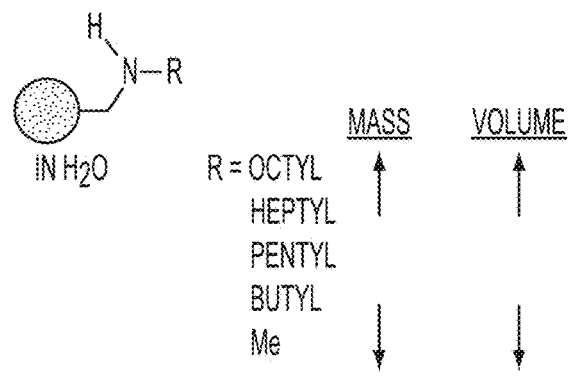
FIG. 7A is a schematic illustration of trends in mass and volume for an alkyl-substituted series of functionalized beads.
Figure 7B:
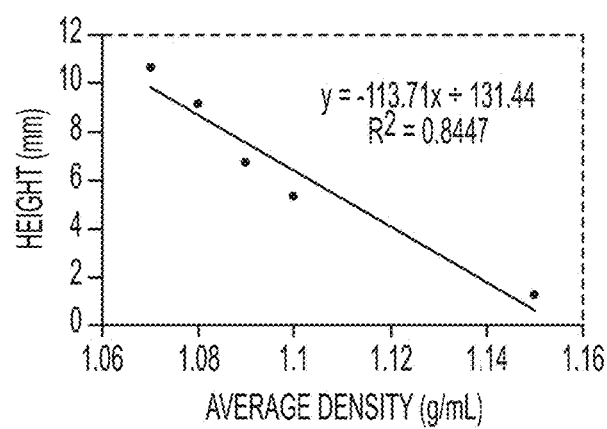
FIG. 7B is a plot of bead location (as measured as distance from a magnetic pole) as a function of molecular weight for the alkyl-substituted series of beads prepared as illustrated in FIG. 7A.

The ability to separate the variously substituted beads is affected by the relative changes in mass and volume that occur upon substitution of the bead. FIG. 7A illustrates the changes in mass and volume that occur in the alkyl amine-substituted series, where R=methyl, butyl, pentyl, heptyl and octyl. In this series at the lower end of the series, both mass and volume are small; not surprisingly, both mass and volume increase with molecular weight. This results in the location vs. density curve shown in FIG. 7B. FIG. 7B illustrates that the addition of hydrocarbons to polymers leads to less dense materials (they levitate higher in the apparatus). The reason for this change is that the polymers change more in volume that they do in mass.

Figure 8A:
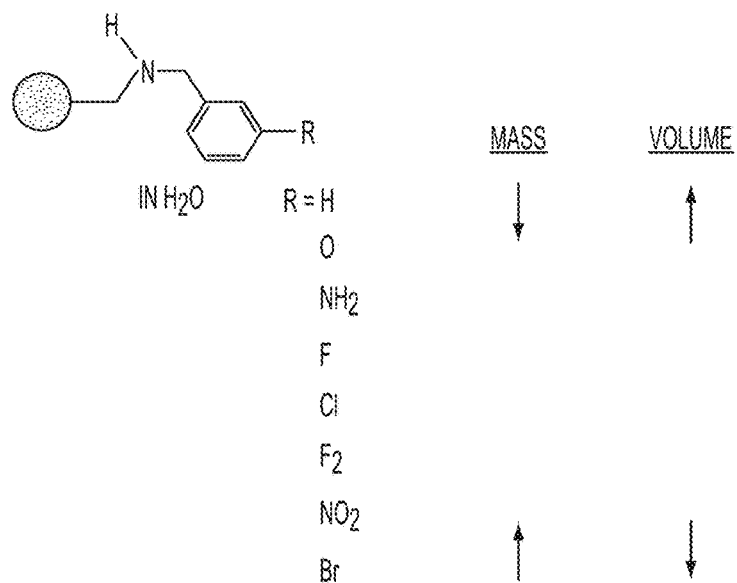
FIG. 8A is a schematic illustration of trends in mass and volume for heteroatom-substituted series of functionalized beads.
Figure 8B:
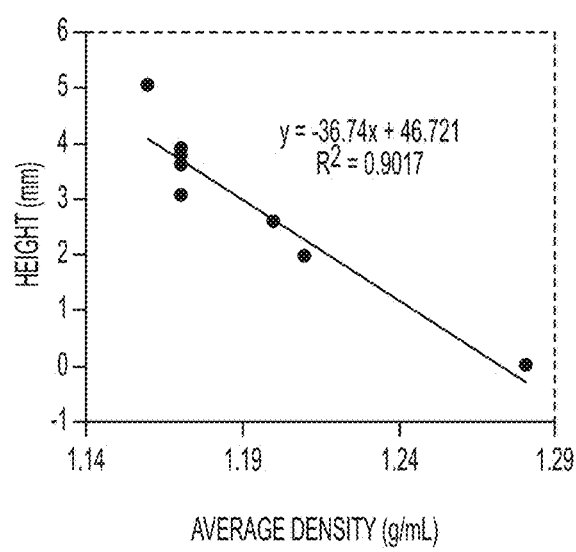
FIG. 8B is a plot of bead location (as measured as distance from a magnetic pole) as a function of molecular weight for the heteroatom-substituted series of beads prepared as illustrated in FIG. 8A.

Series using halogens and heteroatoms exhibit a somewhat different trend, as is illustrated in FIGS. 8A and 8B. For the substitution series shown in FIG. 7A, smaller R-groups tend to have lower mass and higher volume; in contrast high molecular weight substituents such bromide and nitrate, have relatively smaller volumes. This results in a location vs density curve such as shown in FIG. 8B. This figure illustrates the effects of adding heteroatoms and halogens to a polymer: the density of the polymer increases in all cases (and levitates at a lower height); this increase in density is the result of increased mass, but decreased volume.

The trends described in FIGS. 4-8 allow one to predict whether a polymer will levitate lower or higher (than its original state) when it is chemically modified. This predictive capability is useful for monitoring solid phase chemical reactions. One way of monitoring a reaction, is to perform a solid phase reaction (using techniques known to those trained in the art), and then compare the levitation height of the product to the levitation height of the starting material, and the levitation height (if available) of the fully functionalized polymer. A second way to monitor a reaction is to include the reagents for the reaction in the paramagnetic gadolinium solution. The reagents will react with the polymer while it is levitating and the density (and levitation height) will change over time according to the extent of the reaction. The reactions can be carried out in the paramagnetic solution.

Alternatively, the reaction is carried out under optimal reaction conditions using the appropriate reactants and solvents and reaction conditions and times. Aliquots of the reaction mixture can be removed periodically and the bead can be introduced into the paramagnetic solution for density determination. The beads can be prepared as needed for the analysis, including washing to remove reagents and solvents that might otherwise interfere. In one or more embodiments, extraneous to the density determination. The density measurements may indicate the extent of reaction (relative amount of reacted and unreacted polymer beads in the reaction mixture) or the composition of the reaction product (number of bead locations can indicate a number of reaction products or side-products).

Measuring Densities of Small Volumes of Liquids and Irregularly Shaped Solids

All matter has a characteristic density and many physical and chemical processes are accompanied by changes in density. Although magnetic levitation has been used for density-based separations of materials, it has not been developed into a tool for accurate measurement of density of small samples. Accurate measurement of density is necessary in many situations: density sensors are used in the petroleum industry (for checking grade and water content of fuel), in the beverage industry (for determining concentrations of sucrose and alcohol), in the cooking oil industry, in urology (for measuring the specific gravity of urine), in materials science, and in forensic science.

A simple analytical technique for measuring density has been developed that is applicable to a broad range of problems. This technique has at least six useful characteristics: i) it is compatible with many diamagnetic solids and with both aqueous and organic liquids; ii) it is insensitive to shape and volume of the sample, and thus does not require an accurate measurement of either; iii) it is compatible with small volumes ($10^{-12}$-$10^{-6}$ L, with a fundamental limit set at ~$50^{-15}$ L, or a droplet of ~1 µm diameter; this limit is due to Brownian motion); iv) the device is inexpensive (the total cost for the NdFeB permanent magnets is $114 and $GdCl_3$ costs $0.34 per gram); v) it does not require electricity; vi) the device is portable and easy to operate (the prototype device is 15×10×15 cm, though smaller magnets and smaller casings could be used as well).

The device may be useful as a general tool for measuring density. In some embodiments, the device and method is capable of measuring density values of both liquids and solids with the sensitivity and precision of the most advanced instruments, but with the speed and ease of the simplest devices. Some of the unique features of this device include the ability to measure the densities of very small samples and of multiple samples at the same time. The device may be useful as a tool for measuring density as well as the chemical changes that lead to changes in density.

A method for measuring densities of liquids and solids with sensitivities of up to four significant figures (i.e., $\Delta\rho=\pm0.0001$ g/cm$^3$) based on the concept of magnetic levitation is provided. The technique may be used to measure: (i) concentrations of solutes dissolved in various solvents, (ii) densities of small volumes, e.g., less than about 10 µL, less than about 1 µL, or less than about 500 nanoliter volumes of liquids (both organic and aqueous), and (iii) densities of polymers with irregular shapes.

Samples with diameters ≥30 µm, for example, reach a stable, equilibrium levitation height in seconds to minutes, while samples with diameters of ~1 µm take ~48 h to reach an equilibrium height (at 23° C.). The motion of particles at 23° C. that are smaller than 1 µm in diameter is driven largely by Brownian motion and the gravitational and magnetic forces have almost no effect on determining their position between the magnets. The method also is sensitive to temperature, though the effects of temperature can be attenuated by increasing the magnitude of the magnetic forces.

In some embodiments, the method assumes that the magnetic susceptibility of the sample has a negligible affect on the levitation height. Likewise, in samples containing mixtures of diamagnetic chemicals, the contributions of diamagnetic susceptibilities are too small relative to the surrounding paramagnetic medium to have a significant effect on the accuracy of the density values (e.g., $\chi_d$=−70×

$10^{-6}$ cm$^3$/mol for C$_6$H$_5$Cl vs. $\chi_d=-120\times10^{-6}$ cm$^3$/mol for C$_{10}$H$_{22}$), even when the composition of the samples vary.

The relationship between magnetic susceptibility and separation of the initial polymer can be expressed as follows:

$$\rho_{starting\ polymer}-\rho_{product}\propto(\chi_i^{SI}(z_{starting\ polymer}-z_{product}))$$

where $\rho_{starting\ polymer}$ and $\rho_{product}$ are the densities of the starting polymer and the polymer at the end of the reaction, and $z_{starting\ polymer}-z_{product}$ is the separation between starting material and product.

In other embodiments, density of an unknown, for example, a sample containing a mixture of materials A and B, can be determined by comparison of the unknown against a suitable calibration curve.

The invention is described with reference to the following examples, which are provided for the purpose of illustration only and are in no way intended to be limiting of the invention.

EXAMPLE 1

Densities of Particles for Separations in Aqueous Solutions

The useful range of densities in aqueous solution appropriate for the system was explored. The separation range and resolution of a system having the magnetic field distribution illustrated in FIG. 1B using aqueous solutions was investigated using separating solutions containing concentrations of Gd$^{3+}$ from 0.4-1.9 M. A bead of known density (from a set of ~6-mm glass beads with densities ranging from 1.1500-1.8000 g/cm$^3$ (±0.0001 g/cm$^3$)) was placed into a vial filled with an aqueous GdCl$^3$ solution, aligned the vial with the axis of the magnets, and recorded the height (z in FIG. 2) to which the center of the bead levitated (FIG. 2). From these experiments, it was determined that articles with densities up to 1.8 g/cm$^3$ could be levitated at different concentrations of Gd$^{3+}$. This limit was established by maximizing both $\rho_l$ and $\chi_l$ (Equation 2), which maximizes the magnetic force and the buoyancy of the solution. Particles more dense than the Gd$^{3+}$ solution (i.e., $\rho_p>\rho_l$) would levitate at positions below the midway point between the two magnets. By contrast, particles having a density lower than the Gd$^{3+}$ solution (i.e., $\rho_p<\rho_l$) would levitate in the upper half of the space between the magnets and determine the lowest densities that can be levitated in the system.

The difference between the densities of two diamagnetic particles, A and B, is proportional to the magnetic susceptibility of the Gd$^{3+}$ solution ($\chi_l$), and to the difference between their levitation heights, $\rho_A-\rho_B\propto\chi_l(z_A-z_B)$. As a result, for a given difference in density between two diamagnetic particles, the distance between their levitation heights will decrease as the magnetic susceptibility of the solution increases (i.e., as the concentration of gadolinium increases, FIG. 9). The concentration of Gd$^{3+}$ in solution should, therefore, may be chosen to balance two requirements. The magnetic susceptibility of the solution may be: i) sufficient to levitate the particles, but ii) as low as possible to maximize the sensitivity of the system—that is, to maximize the ability of the technique to separate materials with similar densities.

Figure 9:
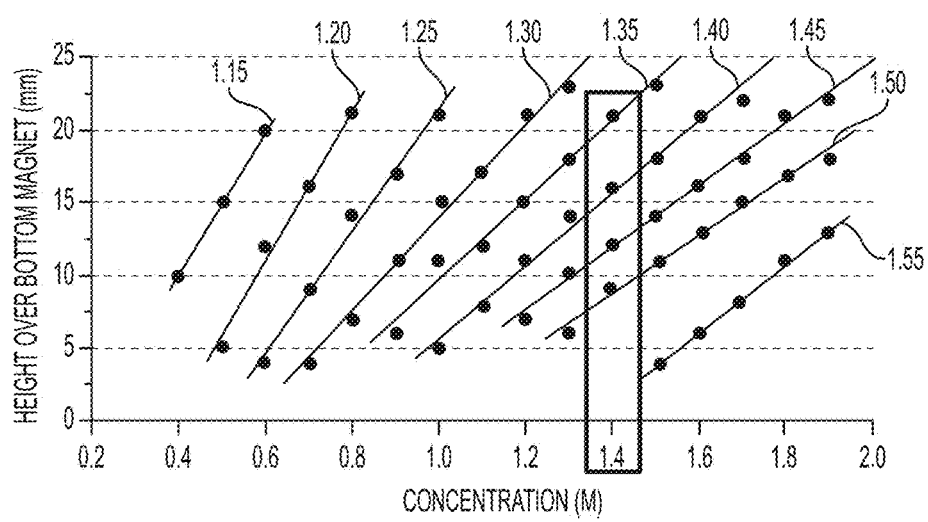
FIG. 9 is a calibration curve for levitation of particles of different densities in $GdCl_3$ solutions over a range of $GdCl_3$ concentrations.

FIG. 9 is a calibration curve for particles with a density range of 1.15-1.60 g/cm$^3$. The system permitted separation of beads with differences in density of 0.05 g/cm$^3$. The sensitivity of the system could be optimized by: i) working at the concentration of gadolinium that maximizes the difference in levitation height, and ii) using a high-resolution optical recording device (camera). The use of digital image processing techniques could help to discriminate closely-positioned materials, and thus further increase the sensitivity of the system.

EXAMPLE 2

Synthesis and Characterization of Gd(DT$_3$)

Figure 10:
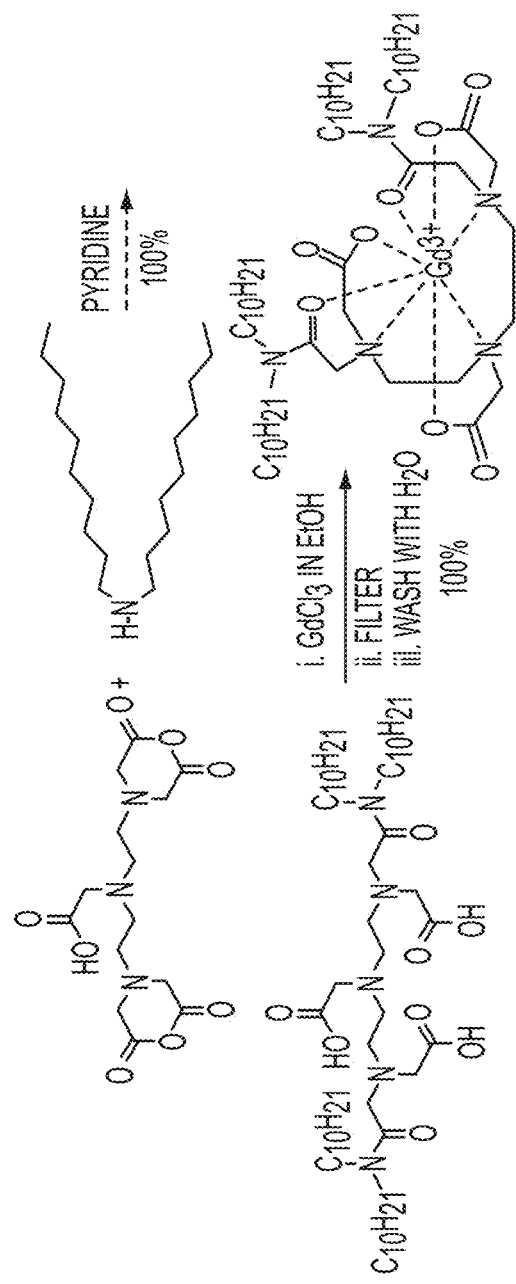
FIG. 10 is a synthetic scheme for the preparation of $Gd(DT_3)$.

Gd(DT$_3$) was prepared in two steps and quantitative yield as described in FIG. 10. The complex is expected to be the nine-coordinate, distorted tri-capped trigonal prism (where water or another solvent molecule is the ninth ligand).

Figure 11:
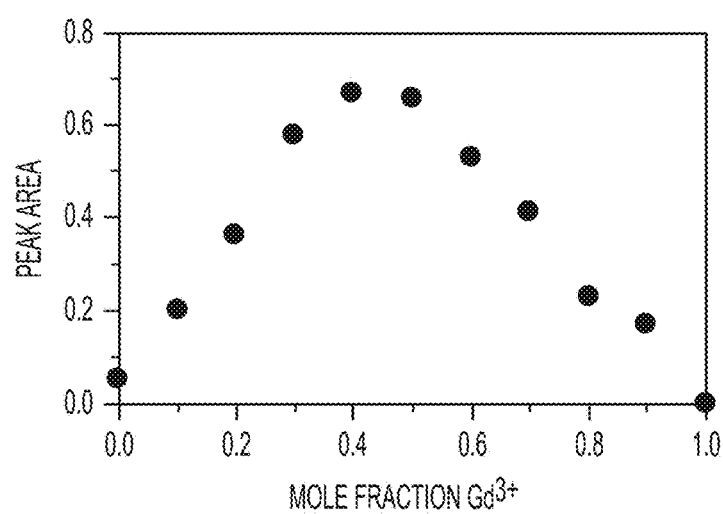
FIG. 11 is a plot of peak area of the $Gd(DT_3)$ by capillary electrophoresis vs. mole fraction of $Gd^{3+}$ and illustrates the Job's plot assay for determination of the stoichiometry of and dissociation constant for $Gd(DT_3)$ in methanol.

The binding affinity of the DT$_3$ ligand for Gd$^{3+}$ and the stoichiometry of the Gd(DT$_3$) complex was determined using capillary electrophoresis (CE). The measurements were performed in methanol at 25° C. and reveals a 1:1 complex between the DT$_3$ ligand and Gd$^{3+}$ with a dissociation constant (K$_d$) of 0.3 µM. See, FIG. 11. The dissociation constant revealed the modest affinity of the DT$_3$ ligand for Gd$^{3+}$ in methanol. Gadolinium(III) chloride (the source of Gd$^{3+}$ for these experiments) is insoluble in non-polar organic solvents; the dissociation constants was not measured in these solvents.

The average magnetic susceptibility for solid Gd(DT$_3$) (in the centimeter-gram-second system of units, cgs (cm$^3$/mol)) was determined by measuring the magnetic susceptibilities for solutions of Gd(DT$_3$) ($\chi_l^{SI}$, International System of Units), and by inputting these values into Equation (3).

$$\chi_l^{SI}=4\pi\chi_l^{CGS}[\text{Gd}^{3+}] \quad (3)$$

The magnetic susceptibility values for the solutions were determined using the magnetic levitation device as shown in FIG. 2.

Figure 12A:
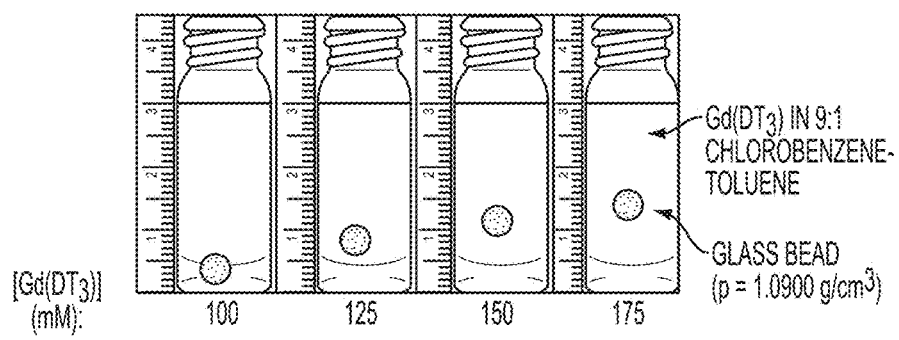
FIG. 12A contains photographs of a 9:1 chlorobenzene: toluene solution containing $GdCl_3$ and glass beads at varying $GdCl_3$ concentrations.

Magnetic susceptibility values were measured for solutions of Gd(DT$_3$) (100-175 mM) in 9:1 chlorobenzene-toluene (23° C.) by levitating a glass bead ($\rho_p=1.0900$ g/cm$^3$) in these solutions (FIG. 12A). This mixture of solvents is adequate because it has a density ($\rho_l=1.082\pm0.003$ g/cm$^3$) slightly below the density of the glass bead that was used. The vertical position of the glass bead (z) in each solution was determined using a ruler, and the densities of the solutions were measured by weighing 1 mL samples. These values (i.e., $\rho_l$, $\rho_p$, and z) were inserted into Equation (1) to calculate the magnetic susceptibility value for each liquid (this calculation assumes that $\chi_p\approx0$).

Figure 12B:
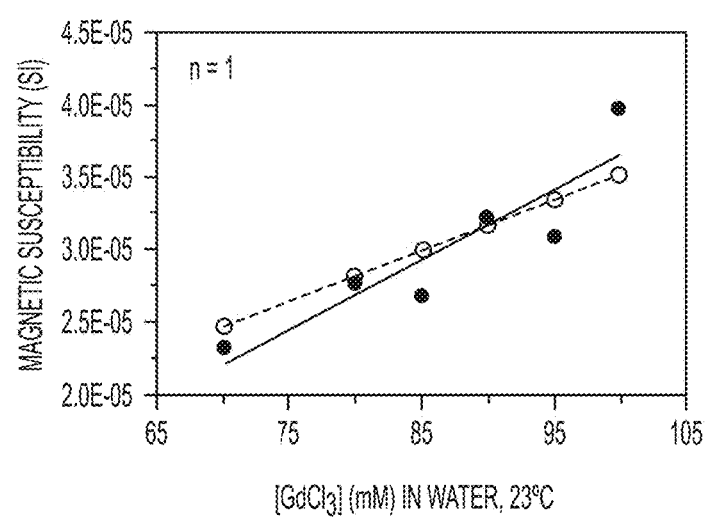
FIG. 12B is a graph of $[GdCl_3]$ in water versus $\chi_i^{SI}$, in which the open circles represent the $\chi_i^{SI}$ values calculated from $\chi_i^{cgs}$ for solid $GdCl_3$, and the closed circles represent the experimental $\chi_i^{SI}$ values obtained from measurements of $\rho_l$ and $z$ and the best fit of the experimental data (using Equation (1)) to the theoretical values.

The remaining variable in Equation (1) that required measuring before the calculation of $\chi_l^{SI}$ could be completed was the strength of the magnetic field at the surface of the magnet (B$_{max}$). The levitation device of FIG. 2 and Equation (1) were used to obtain B$_{max}$ at the surface of the magnet. This value was determined using solutions of GdCl$_3$ (70-100 mM) with known magnetic susceptibilities and by levitating a glass bead ($\rho_p=1.0200$ g/cm$^3$) in these solutions. The densities of the aqueous solutions were determined using the known relationship between [GdCl$_3$] and density (in water), and the $\chi_l^{SI}$ values for the solutions were calculated using Equation (3) (using the $\chi_l^{cgs}$ value for solid GdCl$_3$). The concentration of GdCl$_3$ against the calculated $\chi_l^{SI}$ values is reported in FIG. 12B, and the strength of the magnetic field was determined by fitting Equation (1) with the theoretical $\chi_l^{SI}$ values using experimentally-measured values for z and $\rho_l$, and by varying the strength of the magnetic field (B$_{max}$) and the density of the glass bead ($\rho_p$) in FIG. 12B. The best fit of the experimental values to the predicted line provided a magnetic field strength ($B_{max}$) at the surface of the magnet of 0.3213 T (0.3652 T using a magnetometer) and a density for the glass bead of 1.0204 g/cm³ (a value that is 0.0004 g/cm³ higher than the value supplied by the vendor).

The calibrated value for $B_{max}$ was used to calculate the $\chi_i^{SI}$ values for the solutions of Gd(DT₃) (using Equation (1) and values for $\rho_l$ and z that were measured experimentally). Equation (3) was used to calculate the average $\chi_i^{cgs}$ value from four solutions of Gd(DT³) ($\chi_i^{CGS}$=0.036±0.003 cm³/mol Gd(DT₃)). This molar magnetic susceptibility value is nearly equal to the value for solid GdCl₃ (0.028 cm³/mol GdCl₃).

EXAMPLE 3

Densities of Particles for Separations in Non-Aqueous Solutions

The useful range of densities in non-aqueous solution appropriate for the system was explored. Non-aqueous solutions have different densities than aqueous solutions, and can be used to expand the range of densities of materials that this system is able to separate. This is of interest in the monitoring of chemical reactions, many of which do not occur in aqueous solutions. A methanol solution containing GdCl₃ in various concentrations was used to levitate various polymers with densities between 0.90 and 1.05 g/cm₃: polypropylene (PP), polyethylene (PE), and polystyrene (PS). Methanol is a suitable solvent because i) it has a density of 0.792 g/cm³, a value lower than that of both water and most polymers, ii) it is a good solvent for dissolving inorganic salts (e.g., a solution of 1 M GdCl₃ in methanol), iii) it does not swell PDMS, and iv) it does not dissolve most hydrophobic polymers, including PP, PE, and PS.

Figure 13A:
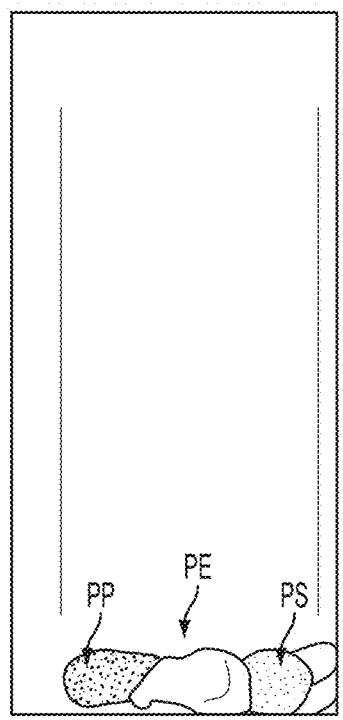
FIG. 13 contains photographs of a methanol solution containing $GdCl_3$ and pieces of PP (poly(propylene)), PE (poly(ethylene)), and PS (poly(styrene)) outside and inside the magnetic field configuration. A) A 360-mM $GdCl_3$ solution in methanol in the absence of the magnetic field. Since this solution was less dense than the polymers, the polymers sank to the floor of the vial. B) In the applied magnetic field, the PP and PE particles levitated while the PS particle remained on the floor of the vial. C) A 435-mM $GdCl_3$ solution in methanol in the absence of a magnetic field. PP was less dense than the solution and it floated at the air/methanol interface. D) The 435-mM $GdCl_3$ solution containing the same polymer pieces (as in FIG. 13C) in an applied magnetic field.
Figure 13B:
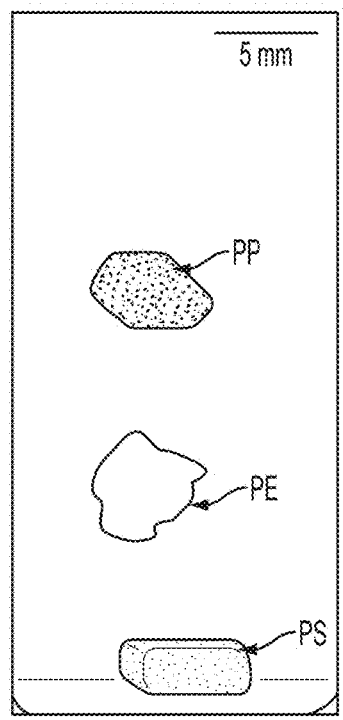

Many common industrial plastics have densities less than that of water—for example, the densities of PP and PE are 0.90 and 0.93 g/cm³, respectively. Thus, most polymers will float when placed in water, making separation less effective. When placed in a vial containing a 360-mM GdCl₃ solution of methanol, all three polymers (PP, PE, and PS (which is more dense than water, $\rho$=1.05 g/cm³)), sank to the bottom of the vial in the absence of an applied magnetic field (FIG. 13A). After aligning the vial with the axis of the magnets, both PP and PE pieces levitated to different heights; the PS did not levitate and remained on the bottom.

Figure 13C:
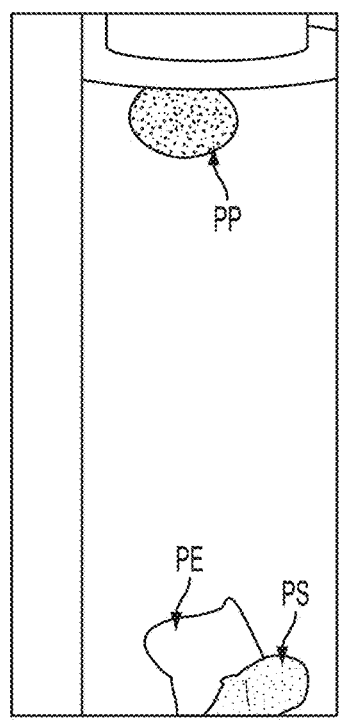
Figure 13D:
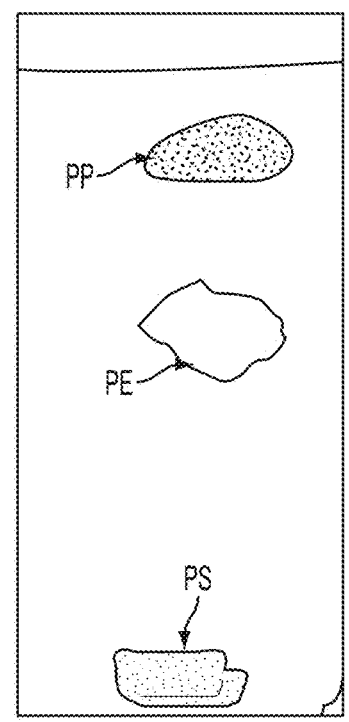

An interesting physical phenomenon occurred when a piece of PP, PE, and PS was placed in a 435-mM GdCl₃ solution in methanol. In the absence of a magnetic field, PS and PE sank to the bottom of the vial, but PP—the least dense polymer—floated at the air/methanol interface (FIG. 13C). When the vial was aligned with the axis of the magnets, PE levitated and the more dense PS remained on the bottom of the vial as expected, but surprisingly the magnetic force pulled the PP into the solution (FIG. 13D). As reported previously, this apparent enhancement of the gravitational force is due to the negative sign of the z-component of the magnetic field above the midway point between the two magnets. Equation 2 and FIG. 1C show that, if the particle is located above that height, the magnetic force is negative, and acts in the same direction as the gravitational force.

EXAMPLE 4

Method for Distinguishing Differences in Density

The concentration of Gd(DT₃) (i.e., the magnetic susceptibility of the solution) affects the sensitivity of the method for distinguishing changes in density of a polymer due to a chemical reaction. The relationship between magnetic susceptibility and separation of the initial polymer can be expressed as follows:

$$\rho_{starting\ polymer} - \rho_{product} \propto (\chi_i^{SI}) (z_{starting\ polymer} - z_{product})$$

where $\rho_{starting\ polymer}$ and $\rho_{product}$ are the densities of the starting polymer and the polymer at the end of the reaction, and $z_{starting\ polymer} - z_{product}$ is the separation between starting material and product.

As $\chi_i^{SI}$ of a solution decreases, the separation between two polymer beads and, therefore, the sensitivity of the method increases.

Figure 14A:
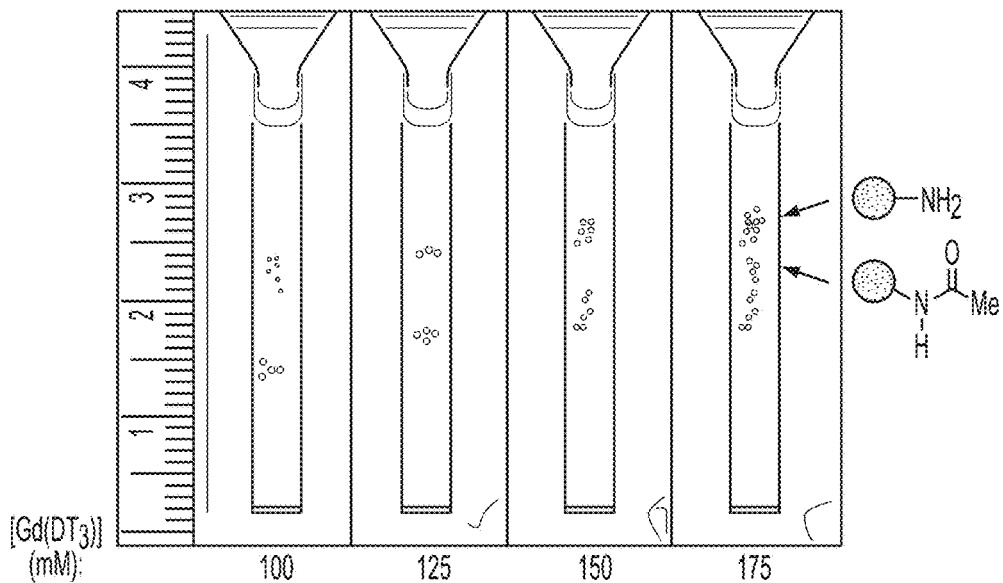
FIG. 14A contains photographs of levitated Tentagel beads (300 µm, 0.27 mmol —$NH_2$/g of polymer, ~3.8 pmol —$NH_2$/bead) with (~five beads) and without acetate groups (~five beads) in 9:1 chlorobenzene-toluene containing different concentrations of Gd($DT_3$) (100-175 mM) at 23° C.
Figure 14B:
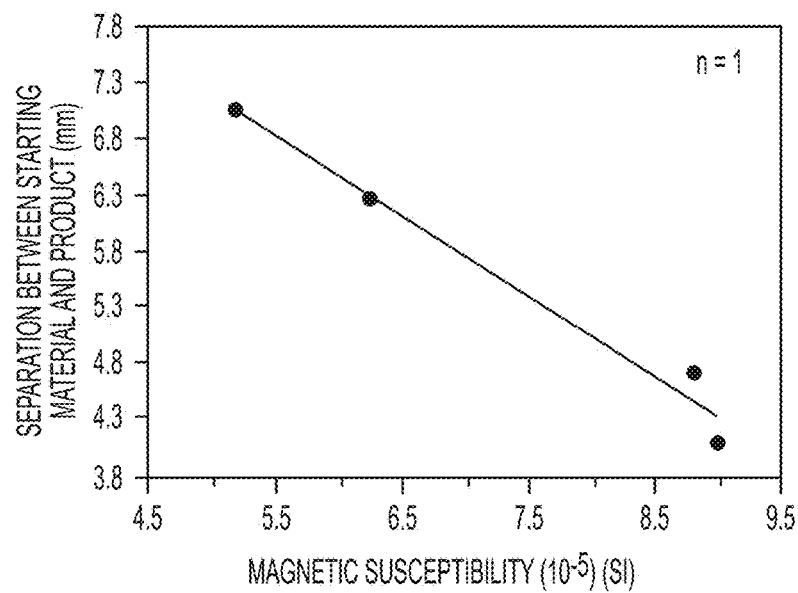
FIG. 14B is a graph of calculated magnetic susceptibility versus separation between starting material (Tentagel-$NH_2$) and product (Tentagel-NHAc).

The sensitivity of the method was demonstrated by levitating (at 23° C.) two polymers with similar densities in solutions of chlorobenzene-toluene (9:1) containing different concentrations of Gd(DT₃): (i) Tentagel polymer beads functionalized with primary amines (300 μm, 0.27 mmol —NH₂/g of polymer, ~3.8 pmol —NH₂/bead) and (ii) the same polymer beads after acetylation of the free amines (FIG. 14A). The higher the Gd(DT₃) concentrations, the greater the buoyancy of the particles overall in the paramagnetic solution. FIG. 14B is a plot of calculated magnetic susceptibility versus separation between starting material (Tentagel-NH₂) and product (Tentagel-NHAc).

When the concentration of Gd(DT₃) is altered, the density of the solvent may be adjusted to maintain the correct levitation distance in a convenient location or range in the solution (although that was not the case for the small changes in concentration shown in FIG. 14A). Because Gd(DT₃) is soluble in many organic solvents, the levitation distance is easily adjusted using mixtures of organic solvents.

EXAMPLE 5

Determination of Density of Liquids

Four 0.4 T NdFeB magnets (5×5×1.25 cm in length, width, and height, respectively, grade N42, $B_r$=1.3-1.32 T (remanence), and $H_c$=875 kA/m (coercivity)) were used to generate two fused magnets (5×5×2.5 cm in length, width, and height). These two sets of magnets were aligned 4.5 cm apart with like poles facing one another to generate a gradient of magnetic field and were positioned in this configuration by gluing them into machined aluminum blocks. This configuration of magnets generated an approximately linear response of the device to the density of the object being measured throughout the entire vertical distance between the magnets. Smaller or larger versions of this device can be designed by varying the size of the magnets and the distance between them.

$Gd^{3+}$ was used as the paramagnetic species for this system because it has one of the highest values for magnetic susceptibility ($\chi_p$=+27930×10⁻⁶ cm³/mol GdCl₃) among the ions, forms clear solutions that permit straightforward visualization of samples, and is relatively inexpensive ($0.34 per g of GdCl₃). An alternative paramagnetic salt is MnCl₂, which has $\chi_p$=+14350×10⁻⁶ cm³/mol MnCl₂, and which would be used at higher concentrations than GdCl₃ ($0.02 per g of MnCl₂)

Temperature also affects the density of the sample, the density and the magnetic susceptibility of the paramagnetic solution, and the solubility of the sample and the Gd3+ in the paramagnetic solution. For convenience, tests were conducted at 23° C., though the methods are compatible with other temperatures as well; the response of the system at other temperatures could be calibrated by levitating an object of known density before performing an analysis. More sophisticated versions of this device could include a thermostat to minimize the need for calibrations.

Individual droplets of organic liquids at 23° C. were injected with a syringe into a vial containing an aqueous solution of $GdCl_3$ and centered the vial between the two NdFeB magnets. Test samples were generated by mixing chlorobenzene with either pentaflurobenzonitrile or decane (0-500 mM); in estimating densities, ideal behavior for the solutions is assumed.

5 µL samples of these solutions were levitated in a 385 mM aqueous solution of $GdCl_3$ that was pre-saturated with chlorobenzene at 23° C. Pre-saturating the aqueous paramagnetic solution limits the dissolution of chlorobenzene into the water. Equation (1) was used to predict the levitation height of the organic liquids. The density values were measured by weighing 1 mL samples of each organic solution. The magnetic susceptibility values were calculated for the 385 mM aqueous solution of $Gd^{3+}$ using the molar magnetic susceptibility for solid $GdCl_3$.

Figure 15:
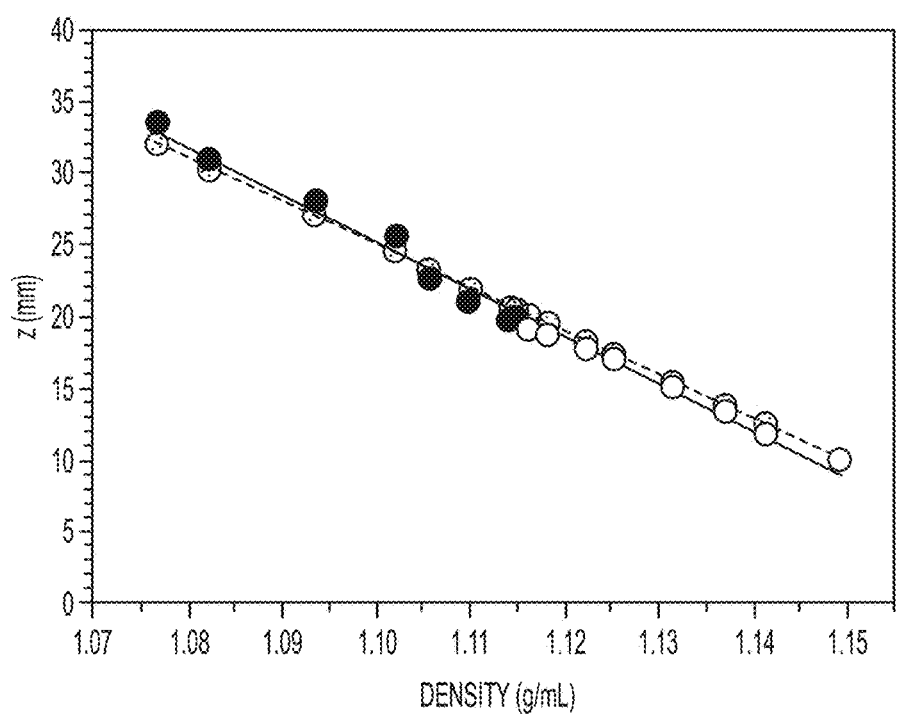
FIG. 15 is a graph correlating the experimentally measured (black and white circles) and theoretically predicted (grey circles) values of z for liquid droplets levitating between two 0.4 T NdFeB magnets.

FIG. 15 plots the predicted (grey) and measured densities for solutions of decane (black) and pentafluorobenzonitrile (white) dissolved in chlorobenzene in a 23° C., 385 mM solution of $GdCl_3$ dissolved in water that was pre-saturated with chlorobenzene ($y=-328x+385$, $R^2=0.990$ represents linear fit to both sets of data, solid line). The error in the vertical position of each droplet is represented by the size of the datum, and is based on the 95% confidence limit from three measurements. The linear least squares fit for the predicted values of levitation height is represented by the dotted line and given by: $y=-301x+355$, $R^2=1$. With these values, theoretical and experimental positions agreed at the 95% confidence level.

Figure 16:
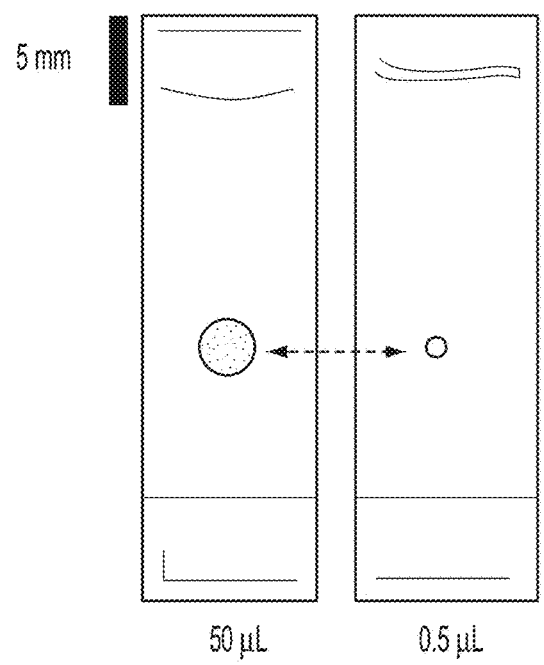
FIG. 16 contain photographs of 50 µL and 0.5 µL droplets of Rhodamine 6G (0.05%) dissolved in chlorobenzene and levitating in 23° C., 385 mM $GdCl_3$ dissolved in water.

In a separate experiment, liquid droplets of separate sizes (volumes) were levitated in order to experimentally determine that densities are independent of the volume of a sample. FIG. 16 shows two droplets with volumes 50 µL and 0.5 µL of Rhodamine 6G (0.05%) dissolved in chlorobenzene levitating at the same height. Though the volumes of the two droplets are different, the levitation heights at the center of each droplet are indistinguishable. The levitation height of the liquid is independent of volume, even for volumes as large as 10 mL; this observation indicates that the magnitude of the magnetic field gradient is constant across the gap between the magnets.

EXAMPLE 6

Measuring Concentrations of Solutes Dissolved in Solvents

The levitation height of the organic droplets provides a measure of the concentration of the solute dissolved in chlorobenzene.

Figure 17A:
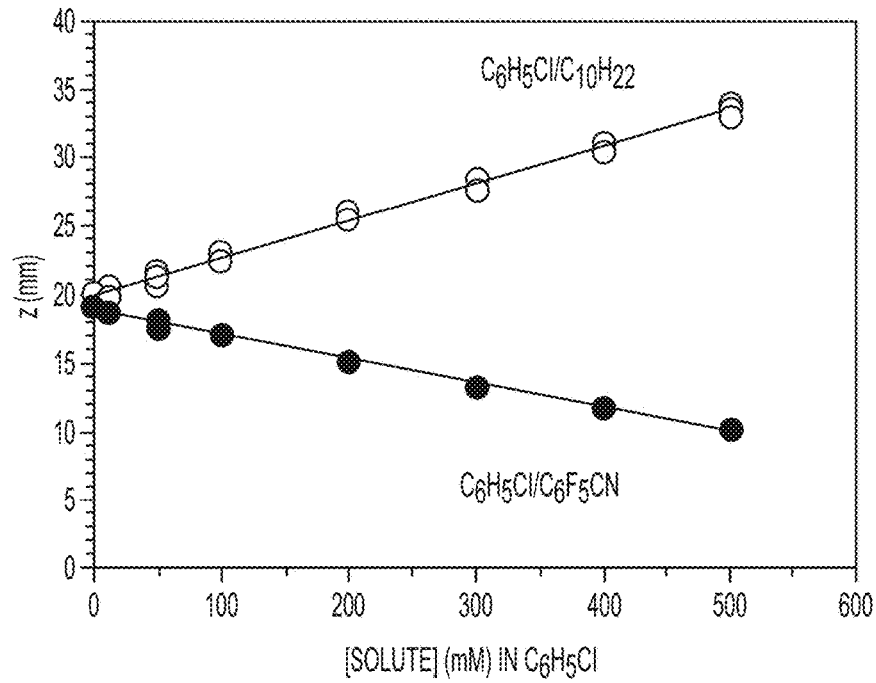
FIG. 17A is a plot of levitation height versus concentration for solutes dissolved in organic solvents and correlating the concentration of two solutes (pentafluorobenzonitrile and decane) and levitation height.

Using the same solutions of chlorobenzene containing pentaflurobenzonitrile or decane (0-500 mM), the concentration of solute in chlorobenzene was plotted versus the levitation height (FIG. 17A). Vertical positions between the magnets (i.e., levitation height, z) were measured by dissolving the solutes in chlorobenzene and by levitating 5 µL aliquots of these solutions at 23° C. in an aqueous solution containing 385 mM $GdCl_3$. Open circles denote decane dissolved in chlorobenzene ($y=0.028x+19.8$, $R^2=0.999$) and closed circles represent pentafluorobenzonitrile in chlorobenzene ($y=-0.018x+18.8$, $R^2=0.998$). This plot gave a linear relationship between the levitation height (z) and the concentration of solute in chlorobenzene. This linear relationship, in principle, can be used to generate a calibration curve for any specific solute/solvent combination. Concentrations of solutes then can be measured by levitating solutions and by comparing their levitation height with the calibration curve.

The magnetic susceptibility of the aqueous $GdCl_3$ solution can be adjusted to control the sensitivity of the system in distinguishing differences in density, and therefore differences in concentrations of solutes.

Figure 17B:
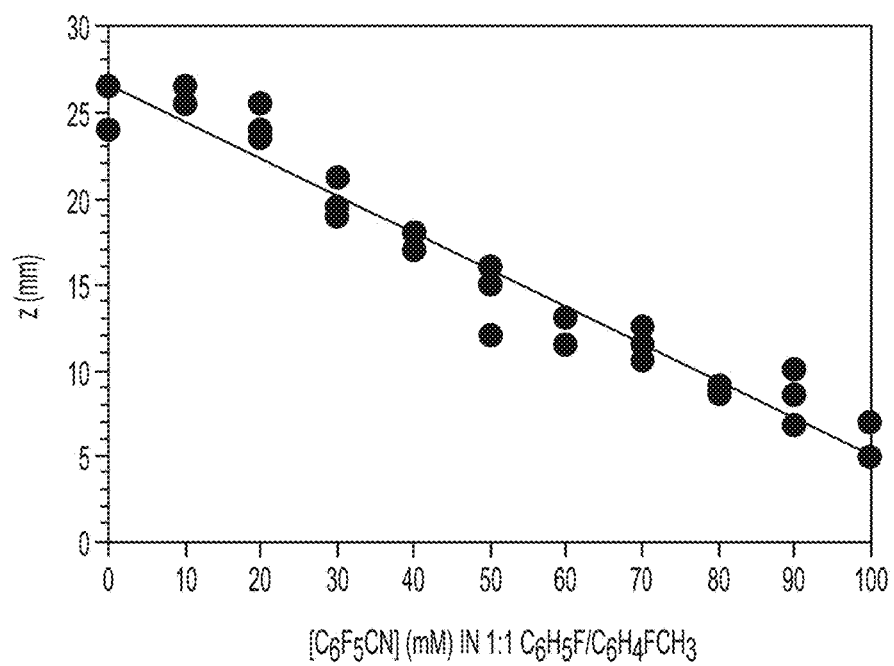
FIG. 17B is a graph correlating the concentration of pentafluorobenzonitrile with levitation height.

The ability to tune the sensitivity of the system to concentration was demonstrated by decreasing the concentration of $GdCl_3$ in water (from 385 mM to 50 mM), and by detecting 0-100 mM pentafluorobenzonitrile dissolved in 1:1 mixture of fluorobenzene and 3-fluorotoluene. For comparison, in 385 mM $GdCl_3$ in water, the dynamic range in concentration is 50-500 mM pentafluorobenzonitrile dissolved in chlorobenzene. To detect concentrations of pentafluorobenzonitrile between 0-100 mM, 5 µL samples of pentafluorobenzonitrile dissolved in a 1:1 mixture of fluorobenzene and 3-fluorotoluene in 50 mM aqueous solutions of $GdCl_3$ saturated with fluorobenzene and 3-fluorotoluene (FIG. 17B) were levitated. The range of concentrations that could be detected was shifted by levitating 5 µL aliquots of pentafluorobenzonitrile dissolved in a 1:1 mixture of fluorobenzene and 3-fluorotoluene in a 23° C. aqueous solution containing 50 mM $GdCl_3$ ($y=-0.216x+26.6$, $R^2=0.969$). The sensitivity of the system can be further increased by lowering the concentration of $GdCl_3$ in water to 10 mM.

In a simple technique for measuring density, the lower limit of resolution in z to be 0.5 mm (a value that can be distinguished easily by eye). This value translates into the following minimum differences in density: 0.002 g/cm$^3$ in 385 mM GdCl3, 0.0002 g/cm$^3$ in 50 mM $GdCl_3$, 0.0001 g/cm3 at 25 mM $GdCl_3$, and 0.00005 g/cm3 at 10 mM $GdCl_3$. While the sensitivity is high at 10 mM $GdCl_3$, in practice the system is too easily perturbed by fluctuations in temperature for it to be useful without stabilization for robust measurements of density. At 25 and 50 mM $GdCl_3$ the system is much less sensitive to external fluctuations in temperature. Higher resolution should be attainable using better optical analysis and greater temperature control.

EXAMPLE 7

Density Values of Aqueous Solutions

The range of solvents that can be levitated is not limited to organic solvents; density values for aqueous droplets can be determined as well. Gadolinium diethylenetriamine triacetic acid tetradecane chelate ($Gd(DT_3)$) is soluble in organic solvents and enables the levitation of droplets of aqueous solvent within them.

Figure 18:
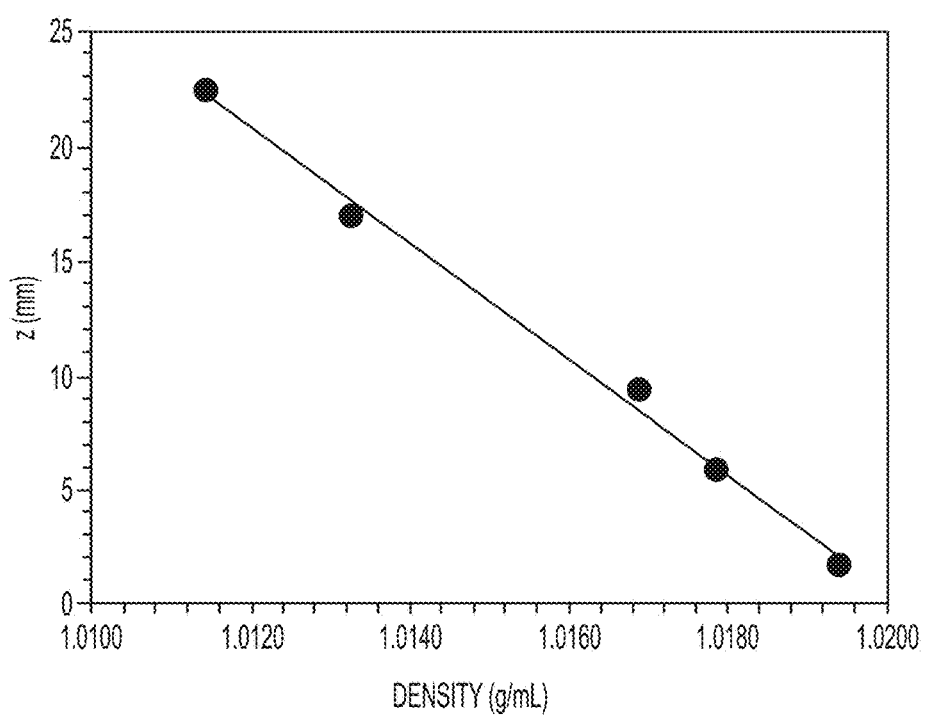
FIG. 18 is a plot of density versus levitation height for aqueous solutions of urea levitated in a 23° C., 50 mM solution of Gd($DT_3$) dissolved in benzonitrile.

1 µL samples of aqueous solutions of urea (500-1000 mM) in 50 mM of $Gd(DT_3)$ dissolved in benzonitrile at 23° C. were levitated. The levitation heights of the aqueous solutions correlate linearly with their densities. FIG. 18 is a plot of density versus levitation height for aqueous solutions of urea levitated in a 23° C., 50 mM solution of $Gd(DT_3)$ dissolved in benzonitrile ($y=-2524x+2576$, $R^2=0.995$). The concentrations of urea vary from 500-1000 mM.

EXAMPLE 8

Measuring Density Values of Polymers with Irregular Shapes

This technique is suitable for measuring densities of polymers as well, and should be useful for solid polymers of irregular shape, for which accurate estimations of volume are difficult.

Four different hydrophobic polymers in aqueous solutions of $GdCl_3$ at 23° C. were evaluated. The polymers were several cubic millimeters in size and varied in shape (e.g., pellets and irregularly-shaped pieces). Each polymer was suspended in an aqueous $GdCl_3$ solution and levitated between the magnets. The levitation height was recorded for the approximate center of mass of each polymer after approximately two minutes. The levitation height of each polymer was used in Equation (1) to estimate the density of the polymer (Table 1). The density values determined by levitation correlate well with those reported in the literature (within the 95% confidence limits).

It is possible to use magnetic levitation to measure the density of four different polymers at the same time. Four different polymers were levitated in one cuvette containing 250 mM $GdCl_3$ dissolved in $H_2O$ and the levitation height was used in Equation (3) to estimate the density of each polymer. The values of density that were obtained for each polymer (polystyrene (measured: 1.045±0.001 g/cm$^3$; literature 1.050 g/cm$^3$); polystyrene($\alpha$-methylstyrene) (measured: 1.060±0.003 g/cm$^3$; literature 1.075 g/cm$^3$); poly(styrene-co-acrylonitrile) (measured: 1.081±0.001 g/cm$^3$; literature 1.080 g/cm$^3$); polystyrene-co-maleic anhydride (measured: 1.106±0.001 g/cm$^3$; literature 1.100 g/cm$^3$) correlated well with the values reported in the literature.

PEGA, and pores of sufficient size for ~70 kDa proteins to access the biotin on the interior of the polymer. The sensitivity of detection depends directly on the loading capacity (i.e., surface density of reacting groups) of the beads and the molecular weight of the bound molecules. In initial experiments, precipitation was observed after adding proteins to the aqueous $Gd^{3+}$ solution, so a Gd3+·DTPA chelate was used instead.

Figure 19A:
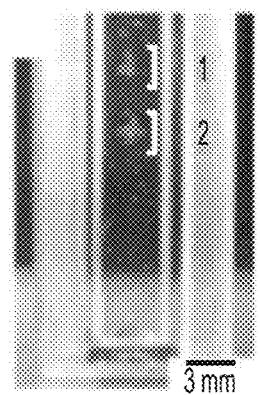
FIG. 19A is an optical image of the separation of biotin-labeled PEGA polymer that was exposed to a solution of streptavidin (2) from a set of biotin-labeled PEGA polymer that was not exposed to streptavidin (1) and FIG. 19B is an optical image of unlabeled PEGA polymer that was exposed to streptavidin mixed with unlabeled PEGA polymer that was not exposed to streptavidin (3).

Binding of streptavidin to solid-supported biotin was detected by incubating ~20 water saturated polymer beads with 20 μL of 0.19-mM protein dissolved in 40-mM potassium phosphate buffer (pH 7.0). After 15 min the solution, was diluted to 1.5 mL to suspend the beads using 210-mM $Gd^{3+}$·DTPA in 40-mM potassium phosphate buffer (pH 7.5), and then added ~20 more biotin-labeled polymer beads. The solution was mixed gently for 5 s with a spatula, and then the cuvette was inserted along the axis of the magnets. After approximately 30 min, all of the beads had clustered into two separate bands (FIG. 19A), the upper one levitating at the same height as the unlabeled PEGA polymer. The lower, denser band reflected the binding of streptavidin to the solid-supported biotin.

Figure 19B:
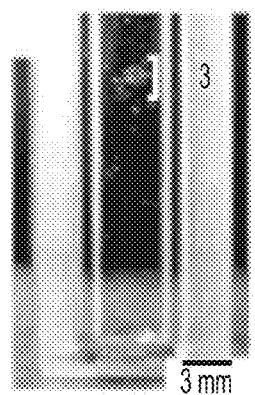

The specific recognition of streptavidin was confirmed using two control experiments: i) the binding experiment was repeated with unlabeled PEGA polymer (FIG. 19B). In this experiment, only the top band was observed, with no obvious non-specific adsorption of streptavidin to the polymer beads; and ii) the binding experiment was repeated using a 1:1 solution of 0.2-mM fluorescein-labeled streptavidin (FITC-streptavidin) and 0.2-mM unlabeled streptavidin dissolved in 40-mM potassium phosphate buffer (not shown). In this case, the beads that were exposed to streptavidin were fluorescent, while the unexposed beads were white.

TABLE 1

Density values of polymers determined by levitation.

| Polymer | Concentration of $GdCl_3$ (mol/L) | Density of $GdCl_3$ solution[a] (g/cm$^3$) | $\chi_{GdCl_3}$ solution[b] (unitless) | Levitation height (z) (mm) | Estimated density[c] (g/cm$^3$) | Density from literature[d] (g/cm$^3$) |
|---|---|---|---|---|---|---|
| Polystyrene | 0.1400 | 1.0321 | 4.908 × 10$^{-5}$ | 8.5 ± 0.9 | 1.050 ± 0.001 | 1.050 |
| Poly(styrene-co-methylmethacrylate) | 0.5300 | 1.1260 | 1.858 × 10$^{-4}$ | 20.9 ± 0.2 | 1.134 ± 0.001 | 1.134 |
| Polymethylmethacrylate | 0.7500 | 1.1780 | 2.630 × 10$^{-4}$ | 21.3 ± 0.2 | 1.186 ± 0.001 | 1.190 |
| Poly(vinylidene fluoride) | 2.1000 | 1.4868 | 7.363 × 10$^{-4}$ | 9.3 ± 0.4 | 1.736 ± 0.007 | 1.740 |

[a]Söhnel, O., and Novotny, P., Densities of Aqueous Solutions of Inorganic Substances, Elsevier, Amsterdam, 1985.
[b]CRC Handbook of Chemistry and Physics, 88th Edition: Magnetic Susceptibility of the Elements and Inorganic Compounds.
[c]Calculated using the levitation height (z) and Equation (1).
[d]Obtained from the vendor.

EXAMPLE 9

Detection of Protein Binding to a Solid-supported Small Molecule

This example demonstrates the detection of density differences as a label-free method for detecting biological binding events. Label-free detection of protein binding was demonstrated by observing the differences in height of levitation of biotin-labeled PEGA polymer (an acryloylated O,O'-bis(2-aminopropyl)polyethylene glycol/dimethylacrylamide copolymer) in the presence and absence of streptavidin, a 53-kDa protein. Beads of biotin-labeled PEGA polymer swell in water (unlike polystyrene-based solid supports), have a loading capacity of 0.2 mmol amine/g

EXAMPLE 10

Figure 20:
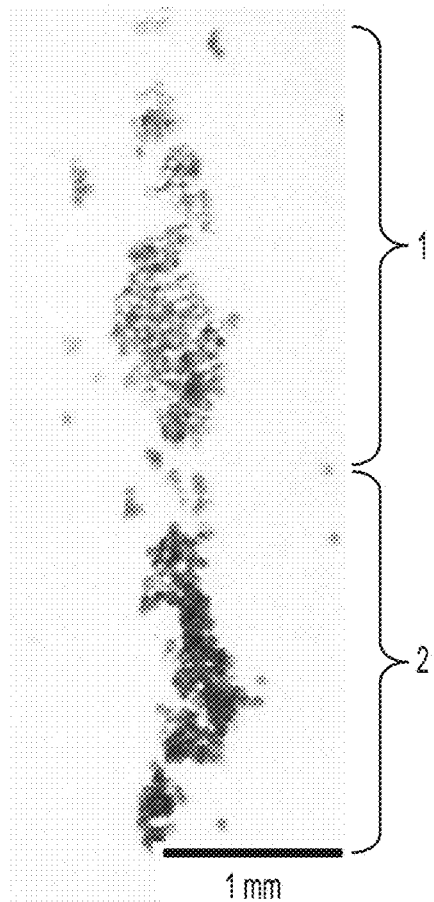
FIG. 20 is a photograph of the separation between microspheres modified with tetraalkylammonium chloride functionality having gold nanoparticles electrostatically attached to the surface (2) and similarly modified microspheres without adsorbed gold (1). The beads with adsorbed gold colloidal particles are denser than those without gold, and therefore they settle lower in the system. The spread in height within each set of beads likely is due to variations in the sizes of the beads (they are polydisperse), which results in varying densities.

Electrostatic Adhesion of Gold Nanoparticles to Chemically Modified Microspheres Gold nanoparticles bound to polymer spheres alter the effective density of the spheres. Magnetic levitation was used to observe the change in density between the gold-bound and gold-free spheres. Crosslinked polystyrene microspheres (~50 μm in diameter) were chemically modified to yield microspheres with tetraalkylammonium chloride functionality (PS—$CH_2NR_3$+Cl—; $NR_3$=quinuclidine); these spheres are positively charged. These spheres were combined in a 1:1 water:DMF solution with gold nanoparticles (~12-nm diameter) capped with a citrate layer; these gold nanoparticles are negatively charged. The nanoparticles condensed onto the surface of the microspheres due to electrostatic attraction; after 1 hour, the microspheres were filtered and collected. In an aqueous, 300-mM solution of $GdCl_3$, the Au-bound spheres were mixed with similar tetraalkylammoniumfunctionalized microspheres that were not bound to Au, and the vial containing this solution was aligned with the axis of the magnets. After the beads reached their equilibrium position (~20 minutes), two distinct bands of beads formed in the system (FIG. 20). The Au-spheres appear purple due to the aggregation of gold nanoparticles. The separation between the two bands is small because the increase in density to a polymer sphere by the attachment of a thin layer of gold nanoparticles is ~0.02 g/cm$^3$. The variation observed in the separation could be due to the amount of gold bound to each sphere, the degree that each sphere was functionalized, or differences occurring in the fabrication of the beads. These results demonstrate that the magnetic levitation device can detect the change in density that accompanies binding of heavy-metal colloids to polymer beads.

EXAMPLE 11

Design of the Microfluidic System

The microfluidic device takes advantage of laminar flow: that is, flow in streams without turbulence that would disrupt separations. Microfluidic systems also use only small volumes of sample and solution. The microfluidic device includes a liquid flow channel that traverses a magnetic field. The fluid flow channel is made of a polymer that is inert to the fluid flowing within. The fluid containing particles to be separated flows into a chamber that is disposed within a magnetic field. Under the force of dynamic flow, the particles are introduced into the chamber in a direction that is substantially orthogonal to the magnetic field. As the particles move into the magnetic field, they migrate to a position in the chamber that is a function of the magnetic field gradient and the particle density. The particles continue to flow through the chamber and pass at the opposite end into one of a plurality of outlet conduits that are positioned along the edge of the chamber in the direction of the magnetic field gradient. The channels carry the particles that have migrated to the characteristic position in the magnetic field into the outlet tube and into a collection vial. In this way, solutions enriched in a specific bead are obtained. The device may be manual or it may be automated. In some embodiments, it may be computer-controlled. The device may be scaled to accommodate samples in a range of sizes and volumes. By changing the size of the separating chamber, the paramagnetic strength of the dynamic fluid and the size and strength of the magnetic field, samples of varying sizes, particle sizes and amounts may be separated.

In a specific example, the microfluidic device consisted of a poly(dimethylsiloxane) (PDMS) replica, fabricated using soft lithography, and sealed to a glass slide. PDMS and the glass slide are transparent and enable straightforward visualization of the separation.

For ease of description, the fluidic system is described in four sections (shown in FIG. 21): the injection system, the separation device, the collection system, and the exhaust.

I) The Injection System: A syringe pump 600 injected the sample from a syringe held vertically (i.e., normal to the lab-bench) at a height (H) above the separation device. This orientation allowed the combination of the fluidic forces and the gravitational forces to direct the beads into the separation device. Other orientations are contemplated, for example, injection may be horizontal. In other embodiments, a pump may be used to create dynamic fluid flow. In the illustrated device, the particles are place in the injection syringe and are introduced into the chamber along with the introduction of the dynamic fluid. In other embodiments, the particles may be introduced in a separation sample injection port. In other embodiments, gravity-driven flow may be used exclusively; this change would enable the system to run without electricity.

II) The Separation Device: The separation chamber 610 was placed vertically (z-direction) between the magnets, with its wide edge aligned with the axis of the magnets. The channel is shown in 3-D perspective view in the insert. While other shapes are contemplated, the triangular shape of the channel minimized regions with low or zero flow rate (i.e., dead volume) so that all particles would flow from a single inlet to multiple outlets across the separation device. In the absence of flow, the diamagnetic particles would levitate along this axis, as discussed previously.

The laminar flow through the channel has both y- and z-components because of the triangular shape of the channel; this additional z-component to the total force creates a slight difference in the observed height between the static mode and flowing mode. 75-150 μm spheres were separated over a range of flow rates from 0.10-0.25 mL/min. For sample volumes ranging from ~100 μL to several mL, these flow rates yielded separation times from minutes to over an hour, respectively. The flow rates were selected so that the time required for the beads to flow across the separation device was longer than that required for the system to reach equilibrium in the magnetic field; in this laminar, quasi-equilibrium protocol, the beads separate in the applied magnetic field before they reach the outlet of the microfluidic device.

III) The Collection System: The collection system removes samples from the device. After passing through the separation device, the only forces acting on the particles are fluidic forces and gravity. Fluid exits the separation chamber 610 through a plurality of outlet tubes 620. Every outlet tube 620 from the PDMS separation device leads to a separate glass vial 630 with a septum top 640 to maintain a sealed fluidic system. These vials were positioned lower than the device to facilitate gravitational settling of the beads and to enhance the rate of collection into the glass vials and minimize clogging of the tubing. Easy removal of the septum tops from the vials permitted simple collection of each sample after the experiment was complete without disrupting the tubing or the fluidic connections.

IV) The Exhaust System: The exhaust system maintains a constant flow rate throughout the entire setup. Each collection vial 630 was attached to an exhaust tube 650 that remained open to the atmosphere. In some embodiments, the collection vials may simply be open to ambient pressure. The collection vials may be equipped with one-way valves to equalize pressure. The exhaust tubes were held above the device at the same height (H) as the syringe for injection. This configuration provided a constant back pressure to the system and prevented a pressure drop due to gravity between the outlet at the bottom of the device (nearest the lower magnet) and the outlet at the top of the device. This exhaust system ensured that all the outlets experienced the same flow rate.

Optimization of Parameters for the Flowing System by Means of Static-Mode Tests. Before employing the microfluidic system, static experiments characterized the steps needed for sample preparation and to determine experimentally the concentration of $GdCl_3$ for optimal separation between particles.

Merrifield resins, formed by copolymerization of styrene, divinylbenzene, and vinylbenzylchloride, are common substrates for solid-phase synthesis; beads with diameters in the range of 75-150 μm were used. Different batches of Merrifield resins contain different relative amounts of backbone-attached —$CH_2Cl$ groups; these differences are reflected in different chlorine content for each batch (0.38, 1.06, 1.24, or 1.95 mmol Cl/g polymer, for the samples examined here). These differences in chloromethyl functionality result in different mass densities for each batch.

Figure 22A:
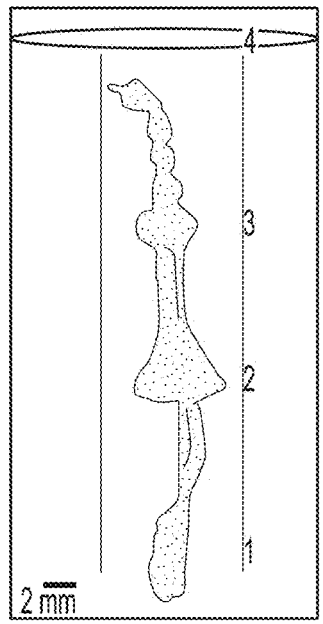
FIG. 22 contains photographs of a static separation of four Merrifield resins with different degrees of functionality (from the bottom to the top of the channel is (1) 1.95, (2) 1.24, (3) 1.06 and (4) 0.38 mmol of Cl/g of polymer). A) Separation of the spheres as received from the manufacturer. B) Separation of the beads after washing and drying them. The densities of the spheres increased and became more uniform. C) Separation of the beads after dyeing them with organic dyes. D) Levitation of three sets of a single batch—0.38 mmol of Cl/g of polymer. Beads of the same batch, but dyed blue or orange, levitate to a similar height as undyed beads.
Figure 22B:
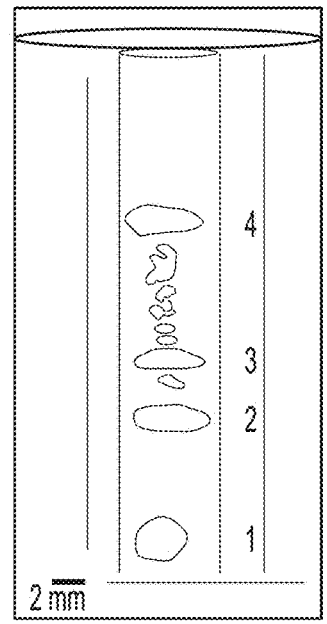
Figure 22C:
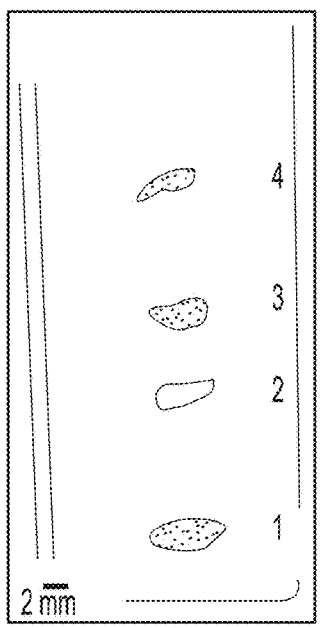
Figure 22D:
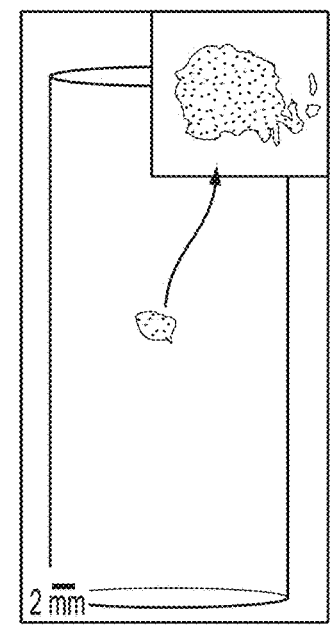

In a solution containing 250-mM $GdCl_3$, all four batches of beads. Merrifield resins taken directly from the vendor were non-uniform in density and yielded broad distributions that complicated the collection of single batches of particles (FIG. 22A). In the magnetic field, the least dense batch of beads (0.38 mmol Cl/g of polymer) floated on the solution/air interface and would not traverse the microfluidic system. To circumvent this problem, the beads were swollen in toluene, rinsed the spheres in ethanol, then in water, and dried them in a 120° C. oven. After this procedure, the density of the spheres became more uniform and slightly greater for all batches (FIG. 22B). The swelling and deswelling process (soaking in toluene followed by rinsing with water) removed any air trapped within the sphere during manufacturing and allowed the polymer to re-organize into a more densely-packed structure.

Dynamic, Flowing Separation and Collection. Having optimized the static separation of four different batches of Merrifield resins, the conditions were transferred to the system using flowing liquids. The system was filled with an aqueous 250-mM GdCl3 solution and introduced the mixture of dyed spheres with a syringe pump. The spheres entered the separation channel from a single inlet on the left (FIG. 23A) and exited through multiple collection outlets on the right (FIG. 23B).

The results of the separation are reported graphically in FIG. 23C. The device is capable of separating all four of the different batches of beads, even when the batches are present in unequal proportions—in FIG. 8, more blue beads are present than any of the other types. The reason that the green spheres, the densest spheres, have the least number of collected particles is because they traversed the separation device along the bottom of the PDMS channel, where some of the beads stuck to the bottom wall of the channel and others were caught at the junction of the outlet tubing and the PDMS microfluidic device.

The separation of particles in a flowing system is a non-equilibrium process: the particles are affected by fluidic, gravitational, and magnetic forces. A particle entering the separation device experiences both fluidic and magnetic forces in the positive y-direction. After a particle passes the axis of the magnets (dotted line in FIGS. 2 and 8A), the By component of the magnetic field becomes negative and thus, the magnetic force (−y direction) opposes the fluidic drag force (+y direction). Some clustering of the particles over the axis of the magnets occurs due to the change in sign of the y-component of the magnetic force (FIG. 8A).

EXAMPLE 12

Measuring Densities of Oils

Aqueous solutions of $GdCl_3$ vary in density from 1.0 to 1.5 g/cm$^3$ (based on the solubility of $GdCl_3$ in water). Since buoyancy contributes to the balance of forces required for levitation, this technique allows levitation and measurement of samples with densities in the range of 1.0-2.0 g/cm$^3$. Gadolinium chloride, however, is soluble in a number of polar organic solvents (e.g., methanol, ethanol, N,N-dimethylformamide, dimethyl sulfoxide). These solvents broaden the range of samples (and densities) that can be measured; the density values for the solvents are: 0.791, 0.789, 0.944, and 1.10 g/mL respectively.

Figure 24A:
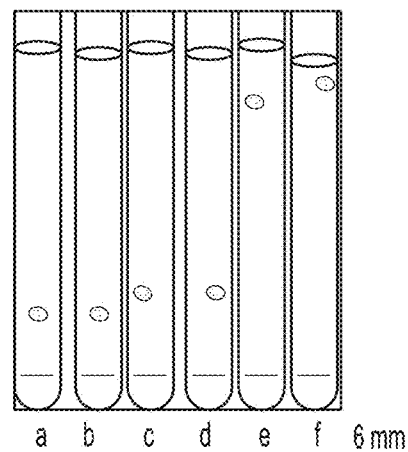
FIG. 24 includes photographs and plots relating densities of oils to vertical position of the oils between the magnets. (A) Photographs showing different types of oils levitating in 300 mM $GdCl_3$ dissolved in methanol; a) Sesame oil, b) Vegetable Oil, c) Olive oil, d) Peanut oil, e) Mineral oil, f) 5W-30 Motor oil. (B) Linear correlation between the levitation height and density (linear least squares fit y=−621x+592, $R^2$=0.98).
Figure 24B:
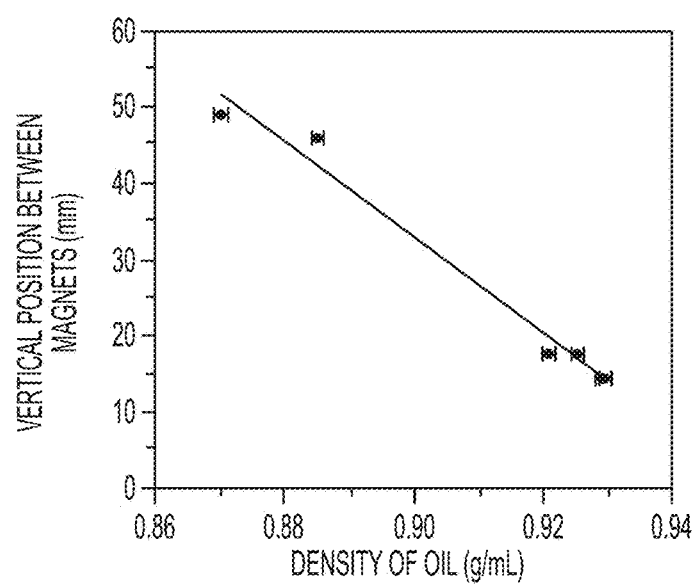

Oils range in density from 0.9-1.0 g/cm$^3$. $GdCl_3$ dissolved in methanol can be used to measure densities of various types of oils. 1 μL samples of different oils were levitated in 300 mM $GdCl_3$ dissolved in methanol. The densities of these oils were correlated with their levitation height and are plotted (FIG. 24). In FIG. 24A, photographs show the levitation distances of different types of oils levitating in 300 mM $GdCl_3$ dissolved in methanol; a) Sesame oil, b) Vegetable Oil, c) Olive oil, d) Peanut oil, e) Mineral oil, f) 5W-30 Motor oil. In FIG. 24B, a plot levitation height and density is shown and a least squares fit of the data is calculated (linear least squares fit y=−621x+592, $R^2$=0.98).

Figure 25A:
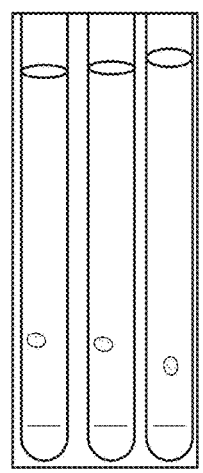
FIG. 25 includes (A) photographs showing changes in pump oil over time. Samples were levitated in 200 mM $GdCl_3$ solution in methanol; (B) linear correlation between the height at which pump oil levitates and days of operation of a vacuum pump; and (C) a schematic showing the procedure used for monitoring the degradation of engine oil.
Figure 25B:
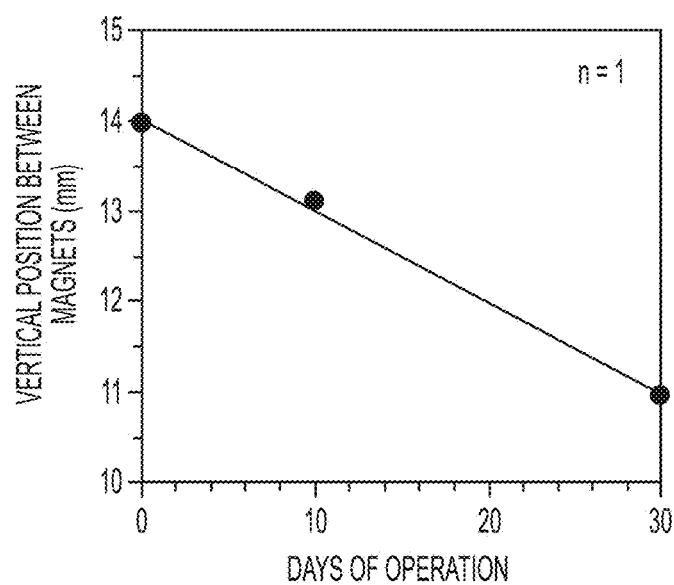
Figure 25C:
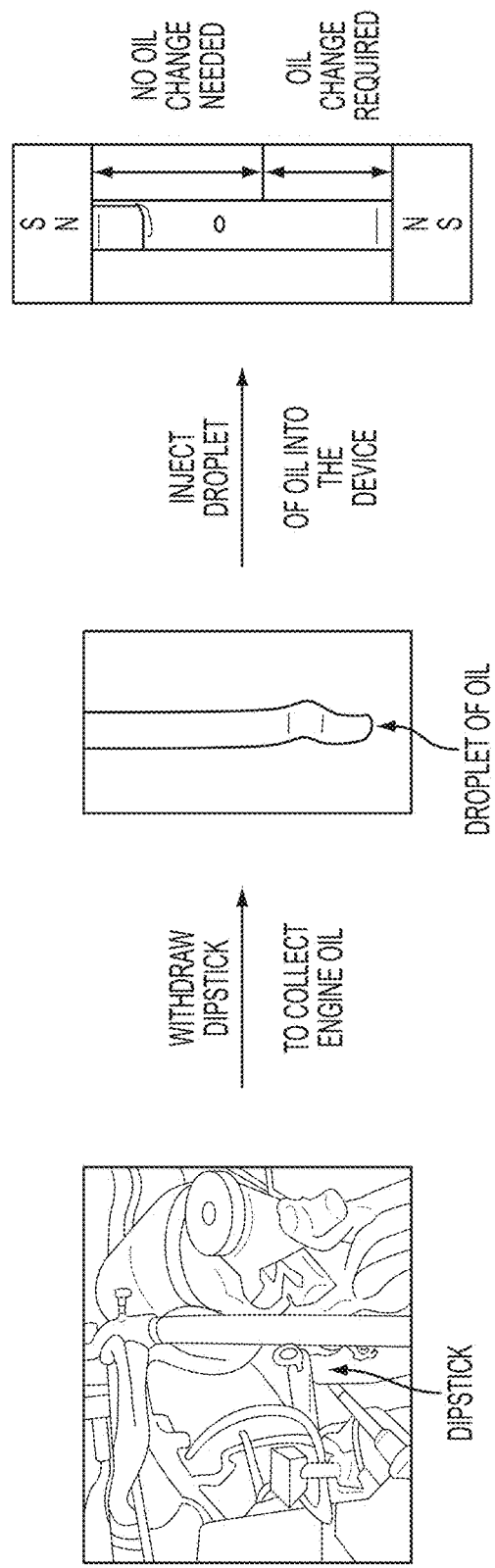

The ability to monitor the degradation of automobile engine oil as a function of the number of miles the vehicle was driven was also evaluated. To test the feasibility oil from a vacuum pump was removed and tested over a 30 hour period (FIG. 25). FIG. 25A contains photographs showing changes in pump oil over time. Samples were levitated in 200 mM $GdCl_3$ solution in methanol. FIG. 25B is a linear correlation between the height at which pump oil levitates and days of operation of a vacuum pump. It is contemplated that such testing could be used as an indication of when engine oil needs to be changed, e.g., as illustrated schematically in FIG. 25C.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A method of detecting differences in density, comprising:
   providing a fluid medium with paramagnetic or superparamagnetic properties;
   introducing a diamagnetic material having a first density into the fluid medium to form a suspension of diamagnetic material in the fluid medium;
   in said suspension, exposing the diamagnetic material to a density modifying agent to form a modified diamagnetic material having a second density; and
   applying a magnetic field to the suspension, said suspension comprising at least the modified diamagnetic material, wherein the unmodified diamagnetic material and the modified diamagnetic material move to different positions in the fluid medium to occupy different positions in the magnetic field and the different positions correlate to a difference in density.

2. The method of claim 1, wherein the modified diamagnetic material is covalently associated with the density modifying agent.

3. The method of claim 2, wherein the diamagnetic material is a polymer particle having a chemically reactive site and the density modifying agent is an organic molecule capable of reacting at the polymer particle reactive site.

4. The method of claim 3, wherein the reactive site is at the surface of the particle.

5. The method of claim 3, wherein the polymer particle is porous and the reactive site is in an internal volume of the particle.

6. The method of claim 3, wherein the density modifying agent comprises a plurality of density modifying agents, each capable of reaction at the polymer particle reactive site and each providing a modified particle having a density different from that of the unmodified particle and from each other.

7. The method of claim 1, wherein the modified diamagnetic material is non-covalently associated with the density modifying agent.

8. The method of claim 7, wherein said non-covalent association is selected from the group consisting of electrostatic, hydrophobic, hydrophilic, ionic and van der Waals attractive associations.

9. The method of claim 1, wherein the diamagnetic material comprises a particle including a surface-bound biomolecule and the density modifying agent is a small molecule that binds to the biomolecule.

10. The method of claim 9, wherein the binding is specific.

11. The method of claim 1, wherein the diamagnetic material comprises a particle including a surface-bound organic moiety and the density modifying agent is a biomolecule that binds to the organic moiety.

12. The method of claim 11, wherein the particle comprises biotin-labeled polymer particles.

13. The method of claim 12 wherein the density modifying agent comprises streptavidin.

14. The method of claim 1, wherein the diamagnetic material comprises a charged particle.

15. The method of claim 14, wherein the density modifying agent comprises a colloidal particle of opposite charge, wherein the density of the charged particle and the colloidal particles are different.

16. The method of claim 15, wherein the colloidal particles comprise heavy metal particles.

17. The method of claim 1, wherein the diamagnetic material comprises a particle and the density modifying agent comprises an organic moiety linked to the particle.

18. The method of claim 17, wherein the density modifying agent comprises a plurality of organic moieties of different densities and wherein the suspension comprises a plurality of modified diamagnetic materials having different densities.

19. The method of claim 1, wherein the fluid medium with paramagnetic or superparamagnetic properties is an aqueous solution.

20. The method of claim 1, wherein the fluid medium with paramagnetic or superparamagnetic properties is a non-aqueous solution.

21. The method of claim 1, wherein the fluid medium with paramagnetic or superparamagnetic properties comprises a gadolinium(III) salt.

22. The method of claim 21, wherein the gadolinium(III) salt comprises gadolinium(III) diethylenetriamine triacetic acid tetradecane.

23. The method of claim 22, wherein the particles are substantially monodisperse.

24. The method of claim 1, wherein the diamagnetic material comprises a particle having a particle size in the range of about 5-5000 µm.

25. The method of claim 1, wherein the magnetic field gradient is linear.

26. The method of claim 1, wherein the magnetic field gradient is linear in a direction along an axis between two magnets generating the magnetic field.

27. The method of claim 1,
wherein the diamagnetic material having a first density comprises a polymer bead functionalized for specific binding with an analyte of interest;
wherein the density modifying agent comprises an analyte of interest; and
wherein the presence of the analyte of interest is determined by detecting a change in position of the polymer bead in the magnetic field.

28. The method of claim 27, wherein introduction of the functionalized polymer bead into the fluid medium with paramagnetic or superparamagnetic properties occurs before exposing the functionalized beads to the sample of interest.

29. The method of claim 28, wherein the population of polymer beads have the same density.

30. The method of claim 29, wherein the particles are substantially monodisperse.

31. The method of claim 28, wherein the population of polymer beads have different densities.

32. The method of claim 27, wherein introduction of the functionalized polymer bead into the fluid medium with paramagnetic or superparamagnetic properties occurs after exposing the functionalized beads to the sample of interest.

33. The method of claim 27, wherein the suspension comprises a population of polymer beads functionalized for specific binding with a plurality of analytes, wherein the presence of a particular analyte is detected by a change in the position of the polymer bead to a new position characteristic of the particular analyte.

34. The method of claim 27, wherein the analyte is selected from the group consisting of proteins, peptides, organic molecules, nucleic acids, oligonucleotides, antibodies, antigens, sugars and carbohydrates.

35. The method of claim 27, wherein the diamagnetic material comprises a particle having a particle size in the range of about 5-5000 µm.

36. The method of claim 27, wherein the magnetic field gradient is linear.

37. The method of claim 27, wherein the magnetic field gradient is linear in a direction along an axis between two magnets generating the magnetic field.

38. The method of claim 1,
wherein the diamagnetic material having a first density comprises a particle linked to a host, and
wherein the density modifying agent comprises a guest that is capable of binding to the host linked particle; and
wherein the particle occupies different equilibrium locations within the magnetic field based on whether a binding complex is formed between the host and the guest.

39. The method of claim 38, wherein the host is selected from the group consisting of proteins, peptides, nucleic acids, organic molecules, inorganic molecule, oligonucleotides, sugars, polysaccharides, antibodies and antigens.

40. The method of claim 39, wherein the guest is selected from the group consisting of proteins, peptides, nucleic acids, organic molecules, inorganic molecule, oligonucleotides, sugars, polysaccharides, antibodies and antigens, wherein the guest is capable of forming a binding complex with the host.

41. The method of claim 40, wherein the solvent comprises an organic solvent.

42. The method of claim 39, wherein the paramagnetic salt comprises gadolinium(III) diethylenetriamine triacetic acid tetradecane.

43. The method of claim 1,
wherein the diamagnetic material having a first density comprises a plurality of particles functionalized with a reactive moiety capable of chemical reaction; and
wherein the density modifying agent comprises entity capable of reacting with the reactive moiety; and
further comprising:
initiating a chemical reaction on the functionalized particles;
applying a magnetic field having a magnetic gradient to the suspension during or after the chemical reaction; and
noting the position of the functionalized particles in the suspension, wherein said position is an indicator of the extent of reaction and/or the composition of a reaction product.

44. The method of claim 43, wherein the paramagnetic salt comprises gadolinium(III) diethylenetriamine triacetic acid tetradecane.

45. The method of claim 44, wherein the solvent comprises an organic solvent.

46. The method of claim 43, wherein portions of particles are removed at selected times during reaction and the position of the functionalized particle is an indication of extent of reaction.

47. The method of claim 1, wherein the fluid medium with paramagnetic or superparamagnetic properties comprises a paramagnetic salt in a solvent.

48. A method of separating particles based on differences in density, comprising:
providing a fluid medium with paramagnetic or superparamagnetic properties;
introducing an individual diamagnetic particle or a plurality of diamagnetic particles into the fluid medium to form a suspension of diamagnetic material in the fluid medium, each particle comprising a polymer core, and a density modifying agent, the agent selected from a group of organic moieties differing by an R-group; and
applying a magnetic field having a magnetic gradient to the suspension, wherein the diamagnetic particles occupy different locations in the magnetic field based upon the density modifying agent.

49. The method of claim 48, wherein the fluid medium with paramagnetic or superparamagnetic properties comprises a paramagnetic salt in a solvent.

* * * * *